(12) United States Patent
Mortlock et al.

(10) Patent No.: US 7,105,669 B1
(45) Date of Patent: Sep. 12, 2006

(54) QUINAZOLINE DERIVATIVES

(75) Inventors: Andrew Austen Mortlock, Macclesfield (GB); Nicholas John Keen, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 413 days.

(21) Appl. No.: 10/088,852

(22) PCT Filed: Sep. 18, 2000

(86) PCT No.: PCT/GB00/03562

§ 371 (c)(1),
(2), (4) Date: Mar. 21, 2002

(87) PCT Pub. No.: WO01/21595

PCT Pub. Date: Mar. 29, 2001

(30) Foreign Application Priority Data

Sep. 21, 1999 (GB) ................................. 9922173.1

(51) Int. Cl.
| C07D 239/88 | (2006.01) |
| C07D 239/93 | (2006.01) |
| A61K 31/517 | (2006.01) |
| A61P 35/00 | (2006.01) |

(52) U.S. Cl. ...................... 544/284; 544/287; 544/293; 544/244; 514/266.2; 514/266.21; 514/266.22; 514/266.23; 514/266.24; 514/266.3; 514/266.4

(58) Field of Classification Search ............. 514/266.4, 514/228.2, 234.8, 252.17, 266.2, 266.21, 514/266.22, 266.23, 266.24, 266.3; 544/58.6, 544/116, 293, 193, 244, 284, 287
See application file for complete search history.

(56) References Cited

FOREIGN PATENT DOCUMENTS

| WO | WO 96/30347 | 10/1996 |
| WO | WO 98/47541 | 10/1998 |
| WO | 2004/013091 | * 2/2004 |

OTHER PUBLICATIONS

PCT/GB00/03562 International Search Report.

* cited by examiner

Primary Examiner—Thomas C. McKenzie

(57) ABSTRACT

A compound of formula (I) or a salt, ester or amide thereof; where X is O, or S, S(O) or S(O)$_2$ or NR$^{10}$ where R$^{10}$ is hydrogen or C$_{1-6}$ alkyl, and R$^1$, R$^2$, R$^3$, R$^4$, R$^5$, R$^6$, R$^7$, R$^8$ and R$^9$ are various specified organic groups. These compounds are inhibitors of aurora 2 kinase, and are useful in the treatment of cancer.

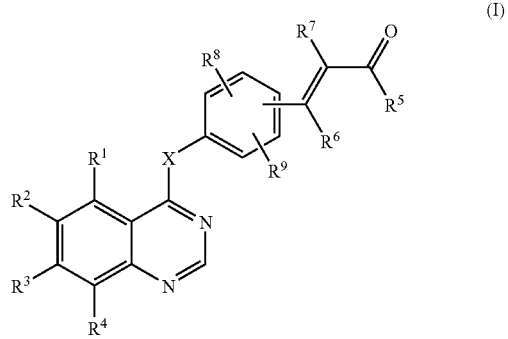

(I)

18 Claims, No Drawings

QUINAZOLINE DERIVATIVES

This application is a US National Stage under 35 U.S.C. § 371 of International Application No. PCT/GB00/03562 (filed Sep. 18, 2000) which claims priority under 35 U.S.C. § 119 (a)–(d) to Application No. GB 9922173.1 filed on Sep. 21, 1999.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672–1677; Pines, 1995, Seminars in Cancer Biology 6: 63–72). Other studies (Loda et al., 1997, Nature Medicine 3(2): 231–234; Gemma et al., 1996, International Journal of Cancer 68(5): 605–11; Elledge et al. 1996, Trends in Cell Biology 6; 388–392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ipl1 proteins. *Drosophila* aurora and *S. cerevisiae* Ipl1, which are highly homologous at the amino acid sequence level, encode serine/threonine protein kinases. Both aurora and Ipl1 are known to be involved in controlling the transition from the G2 phase of the cell cycle through mitosis, centrosome function, formation of a mitotic spindle and proper chromosome separation/segregation into daughter cells. The two human homologues of these genes, termed aurora1 and aurora2, encode cell cycle regulated protein kinases. These show a peak of expression and kinase activity at the G2/M boundary (aurora2) and in mitosis itself (aurora1). Several observations implicate the involvement of human aurora proteins, and particularly aurora2 in cancer. The aurora2 gene maps to chromosome 20q13, a region that is frequently amplified in human tumours including both breast and colon tumours. Aurora2 may be the major target gene of this region, since aurora2 DNA is amplified and aurora2 mRNA overexpressed in greater than 50% of primary human colorectal cancers. In these tumours aurora2 protein levels appear greatly elevated compared to adjacent normal tissue. In addition, transfection of rodent fibroblasts with human aurora2 leads to transformation, conferring the ability to grow in soft agar and form tumours in nude mice (Bischoff et al., 1998, The EMBO Journal. 17(11): 3052–3065). Other work (Zhou et al., 1998, Nature Genetics. 20(2): 189–93) has shown that artificial overexpression of aurora2 leads to an increase in centrosome number and an increase in aneuploidy.

Importantly, it has also been demonstrated that abrogation of aurora2 expression and function by antisense oligonucleotide treatment of human tumour cell lines (WO 97/22702 and WO 99/37788) leads to cell cycle arrest in the G2 phase of the cell cycle and exerts and antiproliferative effect in these tumour cell lines. This indicates that inhibition of the function of aurora2 will have an antiproliferative effect that may be useful in the treatment of human tumours and other hyperproliferative diseases.

A number of quinazoline derivatives have been proposed hitherto for use in the inhibition of various kinases. Examples of such proposals are included in U.S. Pat. No. 5,646,153.

The applicants have found a series of compounds which inhibit the effect of the aurora2 kinase and which are thus of use in the treatment of proliferative disease such as cancer, in particular in such diseases such as colorectal or breast cancer where aurora 2 kinase is known to be active.

The present invention provides a compound of formula (I)

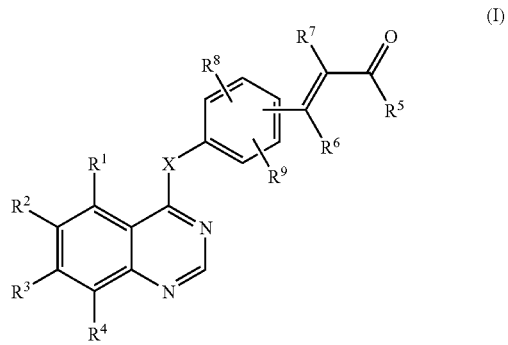

or a salt, ester, amide or prodrug thereof;

where X is O, or S, S(O) or S(O)$_2$ or NR$^{10}$ where R$^{10}$ is hydrogen or C$_{1-6}$alkyl;

R$^5$ is a group OR$^{11}$, NR$^{12}$R$^{13}$ or SR$^{11}$ where R$^{11}$, R$^{12}$ and R$^{13}$ are independently selected from optionally substituted hydrocarbyl or optionally substituted heterocyclic groups, and R$^{12}$ and R$^{13}$ may additionally form together with the nitrogen atom to which they are attached, an optionally substituted aromatic or non-aromatic heterocyclic ring which may contain further heteroatoms, R$^6$ and R$^7$ are independently selected from hydrogen or hydrocarbyl, in particular C$_{1-4}$alkyl;

$R^8$ and $R^9$ are independently selected from hydrogen, halo, $C_{1-4}$alkyl, $C_{1-4}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and $R^1$, $R^2$, $R^3$, $R^4$ are independently selected from halogeno, cyano, nitro, $C_{1-3}$alkylsulphanyl, —N(OH)$R^{14}$ (wherein $R^{14}$ is hydrogen, or $C_{1-3}$alkyl), or $R^{16}X^1$— wherein $X^1$ represents a direct bond, —O—, —$CH_2$—, —OC(O)—, —C(O)—, —S—, —SO—, —$SO_2$—, —$NR^{17}$C(O)—, —C(O)$NR^{18}$—, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl), and $R^{16}$ is hydrogen, optionally substituted hydrocarbyl, optionally substituted heterocyclyl or optionally substituted alkoxy.

These compounds have activity as inhibitors of aurora 2 kinase.

In this specification the term 'alkyl' when used either alone or as a suffix includes straight chained, branched structures. Unless otherwise stated, these groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocyclic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynyl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term "functional group" refers to reactive substituents such as nitro, cyano, halo, oxo, =$CR^{78}R^{79}$, $C(O)_xR^{77}$, $OR^{77}$, $S(O)_yR^{77}$, $NR^{78}R^{79}$, $C(O)NR^{78}R^{79}$, $OC(O)NR^{78}R^{79}$, =$NOR^{77}$, —$NR^{77}C(O)_xR^{78}$, —$NR^{77}CONR^{78}R^{79}$, —N=$CR^{78}R^{79}$, $S(O)_yNR^{78}R^{79}$ or —$NR^{77}S(O)_yR^{78}$ where $R^{77}$, $R^{78}$ and $R^{79}$ are independently selected from hydrogen, optionally substituted hydrocarbyl, optionally substituted heterocyclyl or optionally substituted alkoxy, or $R^{78}$ and $R^{79}$ together form an optionally substituted ring which optionally contains further heteroatoms such as oxygen, nitrogen, S, S(O) or $S(O)_2$, where x is an integer of 1 or 2, y is 0 or an integer of 1–3.

Suitable optional substituents for hydrocarbyl, heterocyclyl or alkoxy groups $R^{77}$, $R^{78}$ and $R^{79}$ as well as rings formed by $R^{78}$ and $R^{79}$ include halo, perhaloalkyl such as trifluoromethyl, mercapto, thioalkyl, hydroxy, carboxy, alkoxy, heteroaryl, heteroaryloxy, cycloalkyl, cycloalkenyl, cycloalkynyl, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_yR^{90}$ where y is as defined above and $R^{90}$ is a hydrocarbyl group such as alkyl.

In particular, optional substituents for hydrocarbyl, hetercyclyl or alkoxy groups $R^{77}$, $R^{78}$ and $R^{79}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_yR^{90}$ where y is as defined above and $R^{90}$ is a hydrocarbyl group such as alkyl.

Certain compounds of formula (I) may include a chiral centre and the invention includes all enantiomeric forms thereof, as well as mixtures thereof including racemic mixtures.

In a particular embodiment, in the compounds of formula (I), at least one of $R^1$, $R^2$, $R^3$ and $R^4$ is a group $R^{16}X^1$— where $X^1$ is as defined in claim 1 and $R^{16}$ is selected from one of the following twenty-two groups:

1) hydrogen or $C_{1-5}$alkyl which may be unsubstituted or which may be substituted with one or more functional groups;
2) —$R^aX^2C(O)R^{22}$ (wherein $X^2$ represents —O— or —$NR^{23}$— (in which $R^{23}$ represents hydrogen, or alkyl optionally substituted with a functional group) and $R^{22}$ represents $C_{1-3}$alkyl, —$NR^{24}R^{25}$ or —$OR^{26}$ (wherein $R^{24}$, $R^{25}$ and $R^{26}$ which may be the same or different each represents hydrogen, or alkyl optionally substituted with a functional group));
3) —$R^bX^3R^{27}$ (wherein $X^3$ represents —O—, —C(O)—, —S—, —SO—, —$SO_2$—, —OC(O)—, —$NR^{28}$C(O)—, —$NR^{28}$C(O)O—, —C(O)$NR^{29}$—, C(O)ON$R^{29}$—, —SO$_2$NR$^{30}$—, —NR$^{31}$SO$_2$— or —NR$^{32}$— (wherein R$^{28}$, R$^{29}$, R$^{30}$, R$^{31}$ and R$^{32}$ each independently represents hydrogen, or alkyl optionally substituted with a functional group) and R$^{27}$ represents hydrogen, hydrocarbyl (as defined herein) or a saturated heterocyclic group, wherein the hydrocarbyl or heterocyclic groups may be optionally substituted by one or more functional groups and the heterocyclic groups may additionally be substituted by a hydrocarbyl group);

4) —R$^c$X$^4$R$^{c'}$X$^5$R$^{35}$ (wherein X$^4$ and X$^5$ which may be the same or different are each —O—, —C(O)—, —S—, —SO—, —SO$_2$, —OC(O)—, —NR$^{36}$C(O)—, —NR$^{36}$C(O)O—, —C(O)NR$^{37}$—, —C(O)ONR$^{37}$—, —SO$_2$NR$^{38}$—, —NR$^{39}$SO$_2$— or —NR$^{40}$— (wherein R$^{36}$, R$^{37}$, R$^{38}$, R$^{39}$ and R$^{40}$ each independently represents hydrogen or alkyl optionally substituted by a functional group) and R$^{35}$ represents hydrogen, or alkyl optionally substituted by a functional group);

5) R$^{41}$ wherein R$^{41}$ is a C$_{3-6}$ cycloalkyl or saturated heterocyclic ring (linked via carbon or nitrogen), which cycloalkyl or heterocyclic group may be substituted by one or more functional groups or by a hydrocarbyl or heterocyclyl group which hydrocarbyl or heterocyclyl group may be optionally substituted by one or more functional groups;

6) —R$^d$R$^{41}$ (wherein R$^{41}$ is as defined hereinbefore);
7) —R$^e$R$^{41}$ (wherein R$^{41}$ is as defined hereinbefore);
8) —R$^f$R$^{41}$ (wherein R$^{41}$ is as defined hereinbefore);

9) R$^{42}$ wherein R$^{42}$ represents a pyridone group, an aryl group or an aromatic heterocyclic group (linked via carbon or nitrogen) with 1–3 heteroatoms selected from O, N and S, which pyridone, aryl or aromatic heterocyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups;

10) —R$^g$R$^{42}$ (wherein R$^{42}$ is as defined hereinbefore);
11) —R$^h$R$^{42}$ (wherein R$^{42}$ is as defined hereinbefore);
12) —R$^i$R$^{42}$ (wherein R$^{42}$ is as defined hereinbefore);

13) —R$^j$X$^6$R$^{42}$ (wherein X$^6$ represents —O—, —S—, —SO—, —SO$_2$—, —OC(O)—, —NR$^{47}$C(O)—, —C(O)NR$^{48}$—, C(O)ONR$^{48}$—, —SO$_2$NR$^{49}$—, —NR$^{50}$SO$_2$— or —NR$^{51}$— (wherein R$^{47}$, R$^{48}$, R$^{49}$, R$^{50}$ and R$^{51}$ each independently represents hydrogen, or alkyl optionally substituted with a functional group) and R$^{42}$ is as defined hereinbefore);

14) —R$^k$X$^7$R$^{42}$ (wherein X$^7$ represents —O—, —C(O)—, —S—, —SO—, —SO$_2$—, —OC(O)—, —NR$^{52}$C(O)—, —C(O)NR$^{53}$—, C(O)ONR$^{53}$—, —SO$_2$NR$^{54}$—, —NR$^{55}$SO$_2$— or —NR$^{56}$— (wherein R$^{52}$, R$^{53}$, R$^{54}$, R$^{55}$ and R$^{56}$ each independently represents hydrogen, or alkyl optionally substituted with a functional group) and R$^{42}$ is as defined hereinbefore);

15) —R$^m$X$^8$R$^{42}$ (wherein X$^8$ represents —O—, —C(O)—, —S—, —SO—, —SO$_2$—, —OC(O)—, —NR$^{57}$C(O)—, —C(O)NR$^{58}$—, C(O)ONR$^{58}$—, —SO$_2$NR$^{59}$—, —NR$^{60}$SO$_2$— or —NR$^{61}$— (wherein R$^{57}$, R$^{58}$, R$^{59}$, R$^{60}$ and R$^{61}$ each independently represents hydrogen, hydrogen, or alkyl optionally substituted with a functional group) and R$^{42}$ is as defined hereinbefore);

16) —R$^n$X$^9$R$^{n'}$R$^{42}$ (wherein X$^9$ represents —O—, —C(O)—, —S—, —SO—, —SO$_2$—, —OC(O)—, —NR$^{62}$C(O)—, —C(O)NR$^{63}$—, C(O)ONR$^{63}$—, —SO$_2$NR$^{64}$—, —NR$^{65}$SO$_2$— or —NR$^{66}$— (wherein R$^{62}$, R$^{63}$, R$^{64}$, R$^{65}$ and R$^{66}$ each independently represents hydrogen, hydrogen, or alkyl optionally substituted with a functional group) and R$^{42}$ is as defined hereinbefore);

17) —R$^p$X$^9$—R$^{p'}$R$^{41}$ (wherein X$^9$ and R$^{41}$ are as defined hereinbefore);
18) C$_{2-5}$alkenyl which may be unsubstituted or which may be substituted with one or more functional groups;
19) C$_{2-5}$alkynyl which may be unsubstituted or which may be substituted with one or more functional groups;
20) —R$^t$X$^9$R$^{t'}$R$^{41}$ (wherein X$^9$ and R$^{41}$ are as defined hereinbefore);
21) —R$^u$X$^9$R$^{u'}$R$^{41}$ (wherein X$^9$ and X$^{41}$ are as defined hereinbefore); and
22) —R$^v$R$^{67}$(R$^{v'}$)$_q$(X$^9$)$_r$R$^{68}$ (wherein X$^9$ is as defined hereinbefore, q is 0 or 1, r is 0 or 1, and R$^{67}$ is a C$_{1-3}$alkylene group or a cyclic group selected from divalent cycloalkyl or heterocyclic group, which C$_{1-3}$alkylene group may be substituted by one or more functional groups and which cyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups; and R$^{68}$ is hydrogen, C$_{1-3}$alkyl, or a cyclic group selected from cycloalkyl or heterocyclic group, which C$_{1-3}$alkylene group may be substituted by one or more functional groups and which cyclic group may be substituted by one or more may be substituted by one or more functional groups or by a hydrocarbyl group optionally substituted by one or more functional groups or heterocyclyl groups, or by a heterocyclyl group optionally substituted by one or more functional groups or hydrocarbyl groups);

and wherein R$^a$, R$^b$, R$^c$, R$^{c'}$, R$^d$, R$^g$, R$^j$, R$^n$, R$^{n'}$R$^p$, R$^{p'}$, R$^{t'}$, R$^{u'}$, R$^v$ and R$^{v'}$ are independently selected from C$_{1-8}$alkylene groups optionally substituted by one or more functional groups, R$^e$ R$^h$, R$^k$ and R$^t$ are independently selected from C$_{2-8}$alkenylene groups optionally substituted by one or more functional groups, and R$^f$, R$^i$, R$^m$ and R$^u$ are independently selected from by C$_{2-8}$alkynylene groups optionally substituted by one or more functional groups.

For example, R$^{16}$ is selected from one of the following twenty-two groups:

1) hydrogen or C$_{1-5}$alkyl which may be unsubstituted or which may be substituted with one or more groups selected from hydroxy, oxiranyl, fluoro, chloro, bromo and amino (including C$_{1-3}$alkyl and trifluoromethyl);

2) —R$^a$X$^2$C(O)R$^{22}$ (wherein X$^2$ represents —O— or —NR$^{23}$— (in which R$^{23}$ represents hydrogen, C$_{1-3}$alkyl or C$_{1-3}$alkoxyC$_{2-3}$alkyl) and R$^{22}$ represents C$_{1-3}$alkyl, —NR$^{24}$R$^{25}$ or —OR$^{26}$ (wherein R$^{24}$, R$^{25}$ and R$^{26}$ which may be the same or different each represents hydrogen, C$_{1-5}$alkyl, hydroxyC$_{1-5}$alkyl or C$_{1-3}$alkoxyC$_{2-3}$alkyl));

3) —R$^b$X$^3$R$^{27}$ (wherein X$^3$ represents —O—, C(O)—S—, —SO—, —SO$_2$—, —OC(O)—, —NR$^{28}$C(O)—, —NR$^{28}$C(O)O—, —C(O)NR$^{29}$—, C(O)ONR$^{29}$—, —SO$_2$NR$^{30}$—, —NR$^{31}$SO$_2$— or —NR$^{32}$— (wherein R$^{28}$, R$^{29}$, R$^{30}$, R$^{31}$ and R$^{32}$ each independently represents hydrogen, C$_{1-3}$alkyl, hydroxy C$_{1-4}$alkyl or C$_{1-3}$alkoxy C$_{2-3}$alkyl) and R$^{27}$ represents hydrogen, C$_{1-6}$alkyl, C$_{2-6}$alkenyl, cyclopropyl, cyclobutyl, cyclopentyl, cyclohexyl, phenyl or a 5–6-membered saturated heterocyclic group with 1–2 heteroatoms, selected independently from O, S and N, which C$_{1-6}$alkyl group may bear 1, 2 or 3 substituents selected from oxo, hydroxy, halogeno, cyclopropyl, amino, C$_{1-4}$alkylamino, C$_{1-4}$alkanoyldi-C$_{1-4}$alkylamino, C$_{1-4}$alkylthio, C$_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($R^{b'}$)$_g$D (wherein f is 0 or 1, g is 0 or 1 and D is a cyclic group selected from $C_{3-6}$cycloalkyl group, an aryl group or a 5–6-membered saturated or unsaturated heterocyclic group with 1–2 heteroatoms, selected independently from O, S and N, which cyclic group may bear one or more substituents selected from halo or $C_{1-4}$alkyl));

4) —$R^c X^4 R^{c'} X^5 R^{35}$ (wherein $X^4$ and $X^5$ which may be the same or different are each —O—, C(O), —S—, —SO—, —SO$_2$—, —NR$^{36}$C(O)—, —NR$^{36}$C(O)O—, —C(O)NR$^{37}$—, —C(O)ONR$^{37}$—, —SO$_2$NR$^{38}$—, —NR$^{39}$SO$_2$— or —NR$^{40}$— (wherein $R^{36}$, $R^{37}$, $R^{38}$, $R^{39}$ and $R^{40}$ each independently represents hydrogen, $C_{1-3}$alkyl or $C_{1-3}$alkoxy$C_{2-3}$alkyl) and $R^{35}$ represents hydrogen, $C_{1-3}$alkyl, hydroxy$C_{1-3}$alkyl or $C_{1-3}$alkoxy$C_{2-3}$alkyl);

5) $R^{41}$ (wherein $R^{41}$ is a 4–6-membered cycloalkyl or saturated heterocyclic ring (linked via carbon or nitrogen) with 1–2 heteroatoms, selected independently form O, S and N, which cycloalkyl or heterocyclic group may bear 1 or 2 substituents selected from oxo, hydroxy, halogeno, cyano, $C_{1-4}$alkyl, hydroxy$C_{1-4}$alkyl, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy nitro, amino, $C_{1-4}$alkoxy, $C_{1-4}$hydroxyalkoxy, carboxy, trifluoromethyl, —C(O)NR$^{43}$R$^{44}$, —NR$^{45}$C(O)R$^{46}$ (wherein $R^{43}$, $R^{44}$, $R^{45}$ and $R^{46}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl));

6) —$R^d R^{41}$ (wherein $R^{41}$ is as defined hereinbefore);
7) —$R^e R^{41}$ (wherein $R^{41}$ is as defined hereinbefore);
8) —$R^f R^{41}$ (wherein $R^{41}$ is as defined hereinbefore);
9) $R^{42}$ (wherein $R^{42}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano $C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxy, carboxamido, trifluoromethyl, cyano, —C(O)NR$^{69}$R$^{70}$, —NR$^{71}$C(O)R$^{72}$ (wherein $R^{69}$, $R^{70}$, $R^{71}$ and $R^{72}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ring D (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl));

10) —$R^g R^{42}$ (wherein $R^{42}$ is as defined hereinbefore);
11) —$R^h R^{42}$ (wherein $R^{42}$ is as defined hereinbefore);
12) —$R^i R^{42}$ (wherein $R^{42}$ is as defined hereinbefore);
13) —$R^j X^6 R^{42}$ (wherein $X^6$ represents —O—, —C(O)—, —S—, —SO—, —SO$_2$—, —OC(O)—, —NR$^{47}$C(O)—, —C(O)NR$^{48}$—, C(O)ONR$^{48}$—, —SO$_2$NR$^{49}$—, —NR$^{50}$SO$_2$— or —NR$^{51}$— (wherein $R^{47}$, $R^{48}$, $R^{49}$, $R^{50}$ and $R^{51}$ each independently represents hydrogen, $C_{1-3}$alkyl, hydroxy$C_{1-3}$alkyl or $C_{1-3}$alkoxy$C_{2-3}$alkyl) and $R^{42}$ is as defined hereinbefore);
14) —$R^k X^7 R^{42}$ (wherein $X^7$ represents —O—, C(O), —S—, —SO—, —SO$_2$—, —NR$^{73}$C(O)—, —C(O)NR$^{74}$—, C(O)ONR$^{74}$—, —SO$_2$NR$^{75}$—, —NR$^{76}$SO$_2$— or —NR$^{77}$— (wherein $R^{73}$, $R^{74}$, $R^{75}$, $R^{76}$ and $R^{77}$ each independently represents hydrogen, $C_{1-3}$alkyl, hydroxy$C_{1-3}$alkyl or $C_{1-3}$alkoxy$C_{2-3}$alkyl) and $R^{42}$ is as defined hereinbefore);
15) —$R^m X^8 R^{42}$ (wherein $X^8$ represents —O—, —(CO)—, —S—, —SO—, —SO$_2$—, —NR$^{57}$C(O)—, —C(O)NR$^{58}$—, C(O)ONR$^{58}$—, —SO$_2$NR$^{59}$—, —NR$^{60}$SO$_2$— or —NR$^{61}$— (wherein $R^{57}$, $R^{58}$, $R^{59}$, $R^{60}$ and $R^{61}$ each independently represents hydrogen, $C_{1-3}$alkyl, hydroxy$C_{1-3}$alkyl or $C_{1-3}$alkoxy$C_{2-3}$alkyl) and $R^{42}$ is as defined hereinbefore);
16) —$R^n X^9 R^{n'} R^{42}$ (wherein $X^9$ represents —O—, —C(O)—, —S—, —SO—, —SO$_2$—, —NR$^{62}$C(O)—, —C(O)NR$^{63}$—, C(O)ONR$^{63}$—, —SO$_2$NR$^{64}$—, —NR$^{65}$SO$_2$— or —NR$^{66}$— (wherein $R^{62}$, $R^{63}$, $R^{64}$, $R^{65}$ and $R^{66}$ each independently represents hydrogen, $C_{1-3}$alkyl, hydroxy$C_{1-3}$alkyl or $C_{1-3}$alkoxy$C_{2-3}$alkyl) and $R^{42}$ is as defined hereinbefore);
17) —$R^p X^9$—$R^{p'1} R^{41}$ (wherein $X^9$ and $R^{41}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
20) —$R^t X^9 R^{t'} R^{41}$ (wherein $X^9$ and $R^{41}$ are as defined hereinbefore);
21) —$R^u X^9 R^{u'} R^{41}$ (wherein $X^9$ and $R^{41}$ are as defined hereinbefore); and
22) —$R^v R^{67}(R^{v'})_q (X^9)_r R^{68}$ (wherein $X^9$ is as defined hereinbefore, q is 0 or 1, r is 0 or 1, and $R^{67}$ is a $C_{1-3}$alkylene group or a cyclic group selected from cyclopropyl, cyclobutyl, cyclopentylene, cyclohexylene or a 5–6-membered saturated heterocyclic group with 1–2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl); and $R^{68}$ is hydrogen, $C_{1-3}$alkyl, or a cyclic group selected from cyclopropyl, cyclobutyl, cyclopentyl, cyclohexyl and a 5–6-membered saturated heterocyclic group with 1–2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl $C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$ ($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl));

and wherein $R^a$, $R^b$, $R^{b'}$, $R^c$, $R^{c'}$, $R^d$, $R^g$, $R^j$, $R^n$, $R^n R^p$, $R^{p'}$, $R^{r'}$, $R^{u'}$, $R^v$ and $R^{v'}$ are independently selected from $C_{1-8}$alkylene groups optionally substituted by one or more substituents selected from hydroxy, halogeno, amino, $R^e$ $R^h$, $R^k$ and $R^t$ are independently selected from $C_{2-8}$alkenylene groups optionally substituted by by one or more substituents selected from hydroxy, halogeno, amino, and $R^t$ may additionally be a bond; and $R^f$, $R^i$, $R^m$ and $R^u$ are independently selected from by $C_{2-8}$alkynylene groups optionally substituted by one or more substituents selected from hydroxy, halogeno, amino.

Particular compounds of formula (I) are compounds of formula (IA)

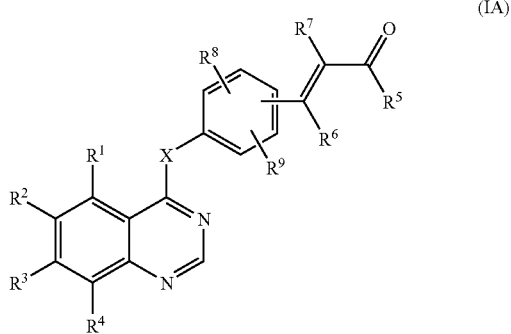

(IA)

or a salt, ester or amide thereof;

where X is O, or S, S(O) or S(O)$_2$, NH or NR$^{10}$ where R$^{10}$ is hydrogen or $C_{1-6}$alkyl,;

$R^5$ is a group OR$^{11}$, NR$^{12}$R$^{13}$ or SR$^{11}$ where R$^{11}$, R$^{12}$ and R$^{13}$ are independently selected from optionally substituted hydrocarbyl or optionally substituted heterocyclic groups, and R$^{12}$ and R$^{13}$ may additionally form together with the nitrogen atom to which they are attached, an aromatic or non-aromatic heterocyclic ring which may contain further heteroatoms, $R^8$ and $R^9$ are independently selected from hydrogen, halo, $C_{1-4}$alkyl, $C_{1-4}$ alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$-alkylcarbamoyl, N,N-di($C_{1-4}$alkyl)carbamoyl, aminosulphonyl, N-$C_{1-4}$-alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and $R^1$, $R^2$, $R^3$, $R^4$ are independently selected from, halo, cyano, nitro, trifluoromethyl, $C_{1-3}$alkyl, —NR$^{14}$R$^{15}$ (wherein R$^{14}$ and R$^{15}$, which may be the same or different, each represents hydrogen or $C_{1-3}$alkyl), or —X$^1$R$^{16}$ wherein X$^1$ represents a direct bond, —O—, —CH$_2$—, —OCO—, carbonyl, —S—, —SO—, —SO$_2$—, —NR$^{17}$CO—, —CONR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, $C_{1-3}$alkyl or $C_{1-3}$alkoxy$C_{2-3}$alkyl), and R$^{16}$ is selected from one of the following seventeen groups:

1') hydrogen or $C_{1-5}$alkyl which may be unsubstituted or which may be substituted with one or more groups selected from hydroxy, fluoro or amino, 2') $C_{1-5}$alkylX$^2$COR$^{22}$ (wherein X$^2$ represents —O— or —NR$^{23}$— (in which R$^{23}$ represents hydrogen, $C_{1-3}$alkyl or $C_{1-3}$alkoxy$C_{2-3}$alkyl) and R$^{22}$ represents $C_{1-3}$alkyl, —NR$^{24}$R$^{25}$ or —OR$^{26}$ (wherein R$^{24}$, R$^{25}$ and R$^{26}$ which may be the same or different each represents hydrogen, $C_{1-3}$alkyl or $C_{1-3}$alkoxy$C_{2-3}$alkyl));

3') $C_{1-5}$alkylX$^3$R$^{27}$ (wherein X$^3$ represents —O—, —S—, —SO—, —SO$_2$—, —OCO—, —NR$^{28}$CO—, —CONR$^{29}$—, —SO$_2$NR$^{30}$—, —NR$^{31}$SO$_2$— or —NR$^{32}$— (wherein R$^{28}$, R$^{29}$, R$^{30}$, R$^{31}$ and R$^{32}$ each independently represents hydrogen, $C_{1-3}$alkyl or $C_{1-3}$alkoxy$C_{2-3}$alkyl) and R$^{27}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkylX$^4$$C_{1-5}$alkylX$^5$R$^{35}$ (wherein X$^4$ and X$^5$ which may be the same or different are each —O—, —S—, —SO—, —SO$_2$—, —NR$^{36}$CO—, —CONR$^{37}$—, —SO$_2$NR$^{38}$—, —NR$^{39}$SO$_2$— or —NR$^{40}$— (wherein R$^{36}$, R$^{37}$, R$^{38}$, R$^{39}$ and R$^{40}$ each independently represents hydrogen, $C_{1-3}$alkyl or $C_{1-3}$alkoxy$C_{2-3}$alkyl) and R$^{35}$ represents hydrogen or $C_{1-3}$alkyl);

5') $R^{41}$ (wherein $R^{41}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);
6') $C_{1-5}$alkyl$R^{41}$ (wherein $R^{41}$ is as defined hereinbefore);
7') $C_{2-5}$alkenyl$R^{41}$ (wherein $R^{41}$ is as defined hereinbefore);
8') $C_{2-5}$alkynyl$R^{41}$ (wherein $R^{41}$ is as defined hereinbefore);
9') $R^{42}$ (wherein $R^{42}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{43}R^{44}$ and —$NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));
10') $C_{1-5}$alkyl$R^{42}$ (wherein $R^{42}$ is as defined hereinbefore);
11') $C_{2-5}$alkenyl$R^{42}$ (wherein $R^{42}$ is as defined hereinbefore);
12') $C_{2-5}$alkynyl$R^{42}$ (wherein $R^{42}$ is as defined hereinbefore);
13') $C_{1-5}$alkyl$X^{6}R^{42}$ (wherein $X^6$ represents —O—, —S—, —SO—, —$SO_2$—, —$NR^{47}CO$—, —$CONR^{48}$—, —$SO_2NR^{49}$—, —$NR^{50}SO_2$— or —$NR^{51}$— (wherein $R^{47}$, $R^{48}$, $R^{49}$, $R^{50}$ and $R^{51}$ each independently represents hydrogen, $C_{1-3}$alkyl or $C_{1-3}$alkoxy$C_{2-3}$alkyl) and $R^{42}$ is as defined hereinbefore);
14') $C_{2-5}$alkenyl$X^{7}R^{42}$ (wherein $X^7$ represents —O—, —S—, —SO—, —$SO_2$—, —$NR^{52}CO$—, —$CONR^{53}$—, —$SO_2NR^{54}$—, —$NR^{55}SO_2$— or —$NR^{56}$— (wherein $R^{52}$, $R^{53}$, $R^{54}$, $R^{55}$ and $R^{56}$ each independently represents hydrogen, $C_{1-3}$alkyl or $C_{1-3}$alkoxy$C_{2-3}$alkyl) and $R^{42}$ is as defined hereinbefore);
15') $C_{2-5}$alkynyl$X^{8}R^{42}$ (wherein $X^8$ represents —O—, —S—, —SO—, —$SO_2$—, —$NR^{57}CO$—, —$CONR^{58}$—, —$SO_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl) and $R^{42}$ is as defined hereinbefore);
16') $C_{1-3}$alkyl$X^{9}C_{1-3}$alkyl$R^{42}$ (wherein $X^9$ represents —O—, —S—, —SO—, —$SO_2$—, —$NR^{62}CO$—, —$CONR^{63}$—, —$SO_2NR^{64}$—, —$NR^{65}SO_2$— or —$NR^{66}$— (wherein $R^{62}$, $R^{63}$, $R^{64}$, $R^{65}$ and $R^{66}$ each independently represents hydrogen, $C_{1-3}$alkyl or $C_{1-3}$alkoxy$C_{2-3}$alkyl) and $R^{42}$ is as defined hereinbefore); and
17') $C_{1-3}$alkyl$X^{9}C_{1-3}$alkyl$R^{41}$ (wherein $X^9$ and $R^{41}$ are as defined hereinbefore).

In particular, $R^6$ and $R^7$ are hydrogen or $C_{1-4}$alkyl such as methyl and are preferably both hydrogen.

Suitable optional substituents for hydrocarbyl groups $R^{11}$, $R^{12}$ or $R^{13}$ as defined in relation to formula (I) include functional groups, and suitable optional substituents for heterocyclic groups $R^{11}$, $R^{12}$ and/or $R^{13}$ include functional groups and hydrocarbyl groups.

Particular examples of $R^5$ are groups $OR^{11}$ where $R^{11}$ is hydrogen or $C_{1-4}$alkyl and in particular is $C_{1-4}$alkyl.

Further examples of $R^5$ are groups of formula $NR^{12}R^{13}$ where one of $R^{12}$ or $R^{13}$ is hydrogen and the other is optionally substituted hydrocarbyl, in particular optionally substituted $C_{1-6}$alkyl, optionally substituted aryl or optionally substituted heterocyclyl.

Particular examples of $R^5$ include groups of formula $NR^{12}R^{13}$ where particular, one of $R^{12}$ or $R^{13}$ is hydrogen and the other is $C_{1-6}$alkyl optionally substituted with one or more groups selected from hydroxy, trifluoromethyl, $C_{1-3}$ alkoxy such as methoxy, cyano, amino, mono- or di-$C_{1-4}$alkylamino, $C_{1-4}$alkylthio such as methylthio, $C_{3-6}$cycloalkyl or heterocyclyl optionally substituted with hydrocarbyl, such as indane, furan, tetrahydrofuran, thiophenyl, any of which heterocyclyl groups may be optionally substituted with $C_{1-4}$ alkyl such as methyl.

In particular, one of $R^{12}$ or $R^{13}$ is hydrogen and the other is $C_{1-6}$alkyl optionally substituted with trifluoromethyl, $C_{1-3}$ alkoxy such as methoxy, cyano, thio$C_{1-4}$alkyl such as methylthio, or heterocyclyl optionally substituted with hydrocarbyl, such as indane, furan optionally substituted with $C_{1-4}$ alkyl such as methyl.

In another embodiment, one of $R^{12}$ or $R^{13}$ is hydrogen and the other is an heterocyclic group such as pyridine, tetrahydropyridine, indane thiophenyl, tetrahydrothiophenyl as well as dioxides thereof, $C_{3-6}$cycloalkyl or a phenyl group; any of which may be optionally substituted with for example one or more groups selected from halo, nitro, alkyl such as methyl, or alkoxy such as methoxy.

In particular, one of $R^{12}$ or $R^{13}$ is hydrogen and the other is an optionally substituted heterocyclic group such as pyridine, or a phenyl group optionally substituted with for example one or more groups selected from halo, nitro, alkyl such as methyl, or alkoxy such as methoxy.

In a further embodiment, $R^5$ is a group $NR^{12}R^{13}$ where $R^{12}$ and $R^{13}$ together with the nitrogen atom to which they are attached an optionally substituted heterocyclic ring, and in particular a non-aromatic ring such as morpholine or piperidine.

Preferably $R^1$ is hydrogen. Suitable $R^4$ is hydrogen or a small substituent such as halo, $C_{1-4}$ alkyl or $C_{1-4}$alkoxy such as methoxy.

Preferably both $R^1$ and $R^4$ are hydrogen.

Preferably $R^2$ and $R^3$ are independently selected from a group —$X^1R^{16}$ where $X^1$ is oxygen and $R^{16}$ is as defined above. Particular groups $R^{16}$ are those in group (1) above, especially alkyl such as methyl or halo substituted alkyl.

In a preferred embodiment, at least one group $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Preferably in this case, $X^1$ is oxygen and $R^{16}$ includes a methylene group directly adjacent $X^1$. Preferably where bridging alkylene, alkenylene or alkynylene groups $R^a$, $R^b$, $R^{b'}$, $R^c$, $R^{c'}$, $R^d$, $R^g$, $R^j$, $R^n$, $R^{n'}R^p$, $R^{p'}$, $R^t$, $R^{u'}$, $R^v$, $R^{v'}$, $R^e$ $R^h$, $R^k$ $R^t$, $R^f$, $R^i$, $R^m$ and $R^u$ are present, at least one such group includes a substituent and in particular a hydroxy substituent.

Suitably $R^3$ is a group $XR^{16}$. Preferably in this case, $X^1$ is oxygen and $R^{16}$ is selected from a group of formula (1), (3), (6) or (10) above and preferably selected from groups (1) or (10) above. Particular groups $R^{16}$ are those in group (1) above, especially alkyl such as methyl or halo substituted alkyl, or those in group (10) above. In one preferred embodiment, at least one of $R^2$ or $R^3$ is a group $OC_{1-5}$alkyl$R^{42}$ and $R^{42}$ is a heterocyclic ring such as an N-linked morpholine ring, so that $OC_{1-5}$alkyl$R^{42}$ may be a group such as 3-morpholinopropoxy.

Other preferred groups for $R^3$ are groups of formula (3) above in particular those where $X^3$ is —$NR^{32}$—.

Suitably $R^2$ is selected from, halo, cyano, nitro, trifluoromethyl, $C_{1-3}$alkyl, —$NR^{14}R^{15}$ (wherein $R^{14}$ and $R^{15}$, which may be the same or different, each represents hydrogen or $C_{1-3}$alkyl), or a group —$X^1R^{16}$. Preferred examples of —$X^1R^{16}$ for $R^2$ include those listed above in relation to $R^3$.

Other examples for $R^2$ and $R^3$ include methoxy or 3,3,3-trifluoroethoxy.

Preferably X is NH or O and is most preferably NH.

Particular examples of groups $R^8$ or $R^9$ include hydrogen, halo, $C_{1-4}$alkoxy such as methoxy, or ethoxy, cyano, trifluoromethyl, or phenyl. Preferably $R^8$ and $R^9$ are hydrogen.

Suitably, at least one substituent is positioned at the 4-position on the phenyl. Thus in a preferred embodiment, the invention provides compounds of formula (IB)

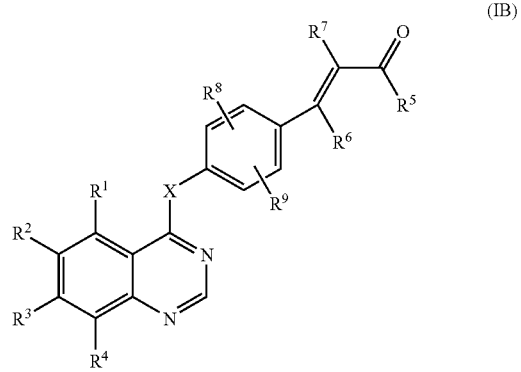

(IB)

where all variable groups are as defined in relation to formula (I) or (IA).

Suitable prodrugs of compounds of formula (I) are groups which enhance solubility and include phoshates and sulphates, in particular phosphates as well as alkyl, aryl or aralkyl derivatives thereof such as dibenzylphosphate. The prodrug moiety may be attached at any suitable position in the molecule, for example as a derivative of a hydroxy group, but in particular, may be advantageously present on one or more of groups $R^1$, $R^2$, $R^3$ or $R^4$, and preferably at $R^2$ or $R^3$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. Where the compound of formula (I) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of formula (I) which have a carboxy group which is derivatised into an amide such as a N-$C_{1-6}$alkyl and N,N-di($C_{1-6}$alkyl)amide such as N-methyl, N-ethyl, N-propyl, N,N-dimethyl, N-ethyl-N-methyl or N,N-diethylamide.

Esters which are not in vivo hydrolysable may be useful as intermediates in the production of the compounds of formula (I).

Particular examples of compounds of formula (I) are set out in Table 1.

TABLE 1

| No | $R^2$ | $R^3$ | X | $R^5$ |
|---|---|---|---|---|
| 1 | $OCH_3$ | $OCH_3$ | NH | ethoxy |
| 2 | $OCH_3$ | $OCH_3$ | O | ethoxy |
| 3 | $OCH_3$ | $OCH_3$ | NH | NH-phenyl |
| 4 | $OCH_3$ | $OCH_3$ | NH | NH-ethyl |
| 5 | $OCH_3$ | $OCH_3$ | NH | 4-morpholino |
| 6 | $OCH_3$ | $OCH_3$ | NH | NH-(4-methylphenyl) |
| 7 | $OCH_3$ | $OCH_3$ | NH | NH-(4-methyl-2-pentyl) |
| 8 | $OCH_3$ | $OCH_3$ | NH | NHCH$_2$-(2-chlorophenyl) |
| 9 | $OCH_3$ | $OCH_3$ | NH | NH-(2,3-dihydroxy-1-propyl) |
| 10 | $OCH_3$ | $OCH_3$ | NH | NH-(2-methyl-1-propyl) |
| 11 | $OCH_3$ | $OCH_3$ | NH | NH-(2-methyl-1-pentyl) |
| 12 | $OCH_3$ | $OCH_3$ | NH | NH-(2-methoxyethyl) |
| 13 | $OCH_3$ | $OCH_3$ | NH | NH-(cyanomethyl) |
| 14 | $OCH_3$ | $OCH_3$ | NH | NH-(3-(dimethylamino)-1-propyl) |
| 15 | $OCH_3$ | $OCH_3$ | NH | NH-(1-n-butyl) |
| 16 | $OCH_3$ | $OCH_3$ | NH | NH-(3-methoxy-2-propyl) |
| 17 | $OCH_3$ | $OCH_3$ | NH | NH-(3-methylphenyl) |
| 18 | $OCH_3$ | $OCH_3$ | NH | NH-(3-methylcyclohexyl) |
| 19 | $OCH_3$ | $OCH_3$ | NH | NH-(2-indanyl) |

TABLE 1-continued

| No | R² | R³ | X | R⁵ |
|---|---|---|---|---|
| 20 | OCH₃ | OCH₃ | NH | NH-(3-chloro-4-(tetrahydrothiophene-1,1'-dioxide)) |
| 21 | OCH₃ | OCH₃ | NH | NHCH₂-(5-methyl-2-furyl) |
| 22 | OCH₃ | OCH₃ | NH | NH-cyclopropyl |
| 23 | OCH₃ | OCH₃ | NH | NH-cyclobutyl |
| 24 | OCH₃ | OCH₃ | NH | NH-cyclopentyl |
| 25 | OCH₃ | OCH₃ | NH | NH-cyclohexyl |
| 26 | OCH₃ | OCH₃ | NH | 1-piperidino |
| 27 | OCH₃ | OCH₃ | NH | NH-(3-pyridyl) |
| 28 | OCH₃ | OCH₃ | NH | NH-(2-methoxyphenyl) |
| 29 | OCH₃ | OCH₃ | NH | NH-(2-methylphenyl) |
| 30 | OCH₃ | OCH₃ | NH | NH-(3-methoxyphenyl) |
| 31 | OCH₃ | OCH₃ | NH | NH-(4-chlorophenyl) |
| 32 | OCH₃ | O-(3-(4-morpholino)-propyl) | NH | OH |
| 33 | OCH₃ | O-(3-(4-morpholino)-propyl) | NH | NHCH₂-cyclohexyl |
| 34 | OCH₃ | O-(3-(4-morpholino)-propyl) | NH | NH-(6-chloro-3-pyridyl) |
| 35 | OCH₃ | O-(3-(4-morpholino)-propyl) | NH | NHCH₂-(2-furyl) |
| 36 | OCH₃ | O-(3-(4-morpholino)-propyl) | NH | NHCH₂-(2-tetrahydrofuryl) |
| 37 | OCH₃ | O-(3-(4-morpholino)-propyl) | NH | NH-(2-pyridyl) |
| 38 | OCH₃ | O-(3-(4-morpholino)-propyl) | NH | NH-(3-pyridyl) |
| 39 | OCH₃ | O-(3-(4-morpholino)-propyl) | NH | NH-(2-methylphenyl) |
| 40 | OCH₃ | O-(3-(4-morpholino)-propyl) | NH | NH-(4-methyl-2-pentyl) |
| 41 | OCH₃ | O-(3-(4-morpholino)-propyl) | NH | NHCH₂CF₃ |
| 42 | OCH₃ | O-(3-(4-morpholino)-propyl) | NH | NH-(2-methyl-1-propyl) |
| 43 | OCH₃ | O-(3-(4-morpholino)-propyl) | NH | NH-(2-methyl-1-pentyl) |
| 44 | OCH₃ | OCH₂C₆H₅ | NH | ethoxy |
| 45 | OCH₃ | O-(3-(4-morpholino)-propyl) | NH | NH-(2-indanyl) |
| 46 | OCH₃ | O-(3-(4-morpholino)-propyl) | NH | NHCH₂CH₂-(2-thiophene) |
| 47 | OCH₃ | O-(3-(4-morpholino)-propyl) | NH | NHCH₂-(5-methyl-2-furyl) |
| 48 | OCH₃ | O-(3-(4-morpholino)-propyl) | NH | NH-(3-(tetrahydrothiophene-1,1'-dioxide)) |
| 49 | OCH₃ | O-(3-(4-morpholino)-propyl) | NH | NH-(2-(thiomethyl)ethyl) |
| 50 | OCH₃ | O-(3-(4-morpholino)-propyl) | NH | ethoxy |
| 51 | OCH₃ | OCH₂CF₃ | NH | NH-(2-(thiomethyl)ethyl) |
| 52 | OCH₃ | OCH₂CF₃ | NH | NH-cyclopentyl |
| 53 | OCH₃ | OCH₂CF₃ | NH | NH-cyclohexyl |
| 54 | OCH₃ | OCH₂CF₃ | NH | NHCH₂-(cyclohexyl) |
| 55 | OCH₃ | OCH₂CF₃ | NH | NH-(6-chloro-3-pyridyl) |
| 56 | OCH₃ | OCH₂CF₃ | NH | NHCH₂-(2-furyl) |
| 57 | OCH₃ | OCH₂CF₃ | NH | NHCH₂-(2-tetrahydrofuryl) |
| 58 | OCH₃ | OCH₂CF₃ | NH | NH-(3-pyridyl) |
| 59 | OCH₃ | OCH₂CF₃ | NH | NH-(2-methylphenyl) |
| 60 | OCH₃ | OCH₂CF₃ | NH | NH—CH₂CF₃ |
| 61 | OCH₃ | OCH₂CF₃ | NH | NH-(2,3-dihydroxy-1-propyl) |
| 62 | OCH₃ | OCH₂CF₃ | NH | NH-(2-methyl-1-pentyl) |
| 63 | OCH₃ | OCH₂CF₃ | NH | NH-(3-methylcyclohexyl) |
| 64 | OCH₃ | OCH₂CF₃ | NH | NH-(2-indanyl) |
| 65 | OCH₃ | OCH₂CF₃ | NH | NHCH₂CH₂-(2-thiophene) |
| 66 | OCH₃ | OCH₂CF₃ | NH | NH-(3-(tetrahydrothiophene-1,1'-dioxide)) |
| 67 | OCH₃ | OCH₂CF₃ | NH | NH-benzyl |
| 68* | OCH₃ | OCH₃ | NH | ethoxy |

\* geometry of double bond is cis (Z) not trans (E)

Compounds of formula (I) may be prepared by various methods which would be apparent from the literature. For example compounds of formula (I) may be prepared by reacting a compound of formula (II)

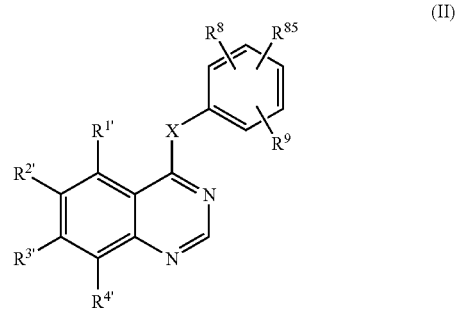

(II)

where X, R⁸ and R⁹ are as defined in relation to formula (I), R¹', R²', R³', R⁴' are groups R¹, R², R³, R⁴ as defined in relation to formula (I) respectively, or precursors thereof; and R⁸⁵ is a leaving group, with a compound of formula (III)

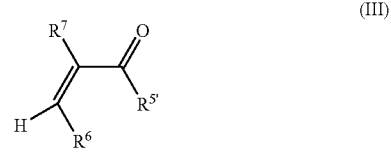

(III)

where R⁶ are R⁷ are as defined in relation to formula (I), R⁵, is a group R⁵ as defined in relation to formula (I) or a precursor group therefore; and thereafter if desired or necessary, converting any precursor groups R¹', R²', R³', R⁴' or $R^{5'}$ to groups $R^1$, $R^2$, $R^3$, $R^4$ or $R^5$ respectively, or changing a group $R^5$ to a different such group.

Suitable leaving groups for $R^{85}$ include halo such as chloro or iodo, mesylate and tosylate. The reaction is suitably effected in the presence of a base such as triethylamine, in an an organic solvent such as acetonitrile or alcohol like isopropanol, at elevated temperatures, conveniently at the reflux temperature of the solvent.

Suitably the compound of formula (III) is prepared in situ, for example by reducing a compound of formula (IV)

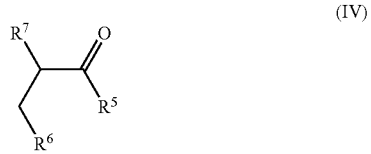

(IV)

where $R^5$, $R^6$ and $R^7$ are as defined in relation to formula (I), with a reducing agent such as tri(o-tolyl)phosphine in the presence of a catalyst such as a palladium catalyst, for instance palladium acetate.

Compounds of formula (II) and (IV) are either known compounds or they can be derived from known compounds by conventional methods.

The conversion of one group $R^5$ to another such group can be readily effected using conventional chemistry. For example compounds of formula (I) where $R^5$ is hydroxy can be converted to amides (where $R^5$ is a group $NR^{12}R^{13}$) using known methods and in particular by reacting the compound of formula (I) where $R^5$ is OH with an amine of formula $HNR^{12}R^{13}$ in the presence of a base such as a carbodiimide.

Conversion of precursor groups $R^{1'}$, $R^{2'}$, $R^{3'}$, $R^{4'}$ or $R^{5'}$ to groups $R^1$, $R^2$, $R^3$, $R^4$ or $R^5$ respectively may be carried out by conventional chemistry. Preferably $R^{1'}$, $R^{2'}$, $R^{3'}$ and $R^{4'}$ are equivalent to groups $R^1$, $R^2$, $R^3$ and $R^4$ respectively so that no conversions are required.

Compounds of formula (I) are inhibitors of aurora 2 kinase. As a result, these compounds can be used to treat disease mediated by these agents, in particular proliferative disease.

According to a further aspect of the invention there is provided a compound of the formula (I) as defined herein, or a salt, ester, amide or prodrug thereof, and in particular a pharmaceutically acceptable salt or an in vivo hydrolysable ester thereof, for use in a method of treatment of the human or animal body by therapy. In particular, the compounds are used in methods of treatment of proliferative disease such as cancer and in particular cancers such as colorectal or breast cancer where aurora 2 is upregulated.

According to a further aspect of the present invention there is provided a method for inhibiting aurora 2 kinase in a warm blooded animal, such as man, in need of such treatment, which comprises administering to said animal an effective amount of a compound of formula (I), or a salt, ester, amide or prodrug thereof, and in particular a pharmaceutically acceptable salt, or an in vivo hydrolysable ester thereof.

The invention also provides a pharmaceutical composition comprising a compound of formula (I) as defined herein, or a salt, ester, amide or prodrug thereof, and in particular a pharmaceutically acceptable salt, or an in vivo hydrolysable ester thereof, in combination with at pharmaceutically acceptable carrier. Preferred compounds of formula (I) for use in the compositions of the invention are as described above.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointenstinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editoral Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of aurora 2 kinase.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

A further aspect of the invention comprises a compound of formula (I) as defined above, or a salt, ester, amide or prodrug thereof, and in particular a pharmaceutically acceptable salt or in vivo hydrolysable ester thereof, for use in the preparation of a medicament for the treatment of proliferative disease. Preferred compounds of formula (I) for this purpose are as described above.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated $DMSOd_6$ (unless otherwise stated) on the delta scale (ppm downfield from tetramethylsilane) using a Varian Gemini 2000 spectrometer operating at a field strength of 300 MHz, or a Bruker DPX300 spectrometer operating at a field strength of 300 MHz; and peak multiplicities are shown as follows: s, singlet; d, doublet; dd, double doublet; t, triplet; q, quartet; qu, quintet; m, multiplet; bs, broad singlet; mass spectrometry (MS) was performed by electrospray on a VG platform;

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Savant AES 2000; column chromatography was performed using either an Anachem Sympur MPLC or Jones Flashmaster MPLC systems on silica using Varian Mega Bond Elut cartridges; the structures of the final products were confirmed by LCMS on a Micromass OpenLynx system using the following and are quoted as retention time (RT) in minutes:

Column: 4.6 mm×3 cm Hichrom RPB
Solvent A: 5% Methanol in Water+0.1% formic acid
Solvent B: 5% Methanol in Acetonitrile+0.1% formic acid
Flow rate: 1.4 ml/min
Run time: 5 minutes with a 4.5 minute gradient from 0–100% B
Wavelength: 254 nm, bandwidth 10 nm
Mass detector: Micromass Platform LC
Injection volume 0.002 ml (vii) Analytical LCMS for compounds which had not been prepared by robotic synthesis was performed on a a Waters Alliance HT system using the following and are quoted as retention time (RT) in minutes:

Column: 2.0 mm×5 cm Phenomenex Max-RP 80A
Solvent A: Water
Solvent B: Acetonitrile
Solvent C: Methanol+1% formic acid
Flow rate: 1.1 ml/min
Run time: 5 minutes with a 4.5 minute gradient from 0–95% B+constant 5% solvent C
Wavelength: 254 nm, bandwidth 10 nm
Injection volume 0.005 ml
Mass detector: Micromass ZMD (viii) Preparative high performance liquid chromatography (HPLC) was performed on a Gilson instrument using the following and are quoted as retention time (RT) in minutes:

Column: 21 mm×10 cm Hichrom RPB
Solvent A: Water+0.1% trifluoroacetic acid,
Solvent B: Acetonitrile+0.1% trifluoroacetic acid
Flow rate: 18 ml/min
Run time: 15 minutes with a 10 minute gradient from 5–100% B
Wavelength: 254 nm, bandwidth 10 nm
Injection volume 2.0–4.0 ml (ix) intermediates were not generally fully characterised and purity was assessed by thin layer chromatography (TLC), HPLC, infra-red (IR), MS or NMR analysis;

The following Examples illustrate the invention.

EXAMPLE 1

Preparation of Compound No. 1 in Table 1

Palladium (II) acetate (303 mg, 1.35 mmol) was added to a solution of 4-(4-iodoanilino)-6,7-dimethoxyquinazoline (6.00 g, 13.5 mmol), ethyl acrylate (1.35 g, 13. 5 mmol) and tri(o-tolyl)phosphine (821 mg, 2.70 mmol) in a mixture of triethylamine (60 ml) and acetonitrile (200 ml) and the reaction heated at reflux for 20 hours under an inert atmosphere. The reaction was cooled to ambient temperature, poured into water (600 ml), diluted with ethyl acetate (200 ml) and filtered through celite. The organic layer was separated, the aqueous was extracted with ethyl acetate (2×200 ml) and the combined organic layers were dried over magnesium sulphate before solvent evaporation in vacuo. Purification by flash chromatography on silica gel, eluting with ethyl acetate, yielded 4-(4-(2-carboethoxy)ethenyl) anilino)-6,7-dimethoxyquinazoline (4.36 g, 85% yield) as a yellow solid:

$^1$H-NMR (DMSO $d_6$): 9.60 (s, 1H), 8.50 (s, 1H), 7.90 (d, 2H), 7.85 (s, 1H), 7.75 (d, 2H), 7.65 (d, 1H), 7.20 (s, 1H), 6.50 (d, 1H), 4.20 (q, 2H), 4.00 (s, 3H), 3.90 (s, 3H), 1.25 (t, 3H):
MS (−ve ESI): 378 (M−H)$^-$,
MS (+ve EDI): 380 (M+H)$^+$.

4-(4-iodoanilino)-6,7-dimethoxyquinazoline, used as the starting material was obtained as follows:

a) A mixture of 4,5-dimethoxyanthranilic acid (19.7 g, 100 mmol) and formamide (10 ml) was heated at 190° C. for 5 hours. The mixture was allowed to cool to approximately 80° C. and water (50 ml) was added. The mixture was then allowed to stand at ambient temperature for 3 hours. Collection of the solid by suction filtration, followed by washing with water (2×50 ml) and drying in vacuo, yielded 6,7-dimethoxy-3,4-dihydroquinazolin-4-one (3.65 g, 18% yield) as a white solid.

$^1$H-NMR (DMSO $d_6$): 12.10 (s, 1H), 7.95 (s, 1H), 7.42 (s, 1H), 7.11 (s, 1H), 3.88 (s, 3H), 3.84 (s, 3H):
MS (−ve ESI): 205 (M−H)$^-$.

b) Dimethylformamide (0.2 ml) was added dropwise to a solution of 6,7-dimethoxy-3,4-dihydro-quinazolin-4-one (10.0 g, 48.5 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with i) saturated aqueous sodium hydrogen carbonate solution (2×250 ml) and ii) brine, and the organic phase was dried over magnesium sulphate. Solvent evaporation in vacuo yielded 4-chloro-6,7-dimethoxyquinazoline (10.7 g, 98% yield) as a white solid:

$^1$H-NMR (DMSO $d_6$): 8.86 (s, 1H), 7.42 (s, 1H), 7.37 (s, 1H), 4.00 (s, 3H), 3.98 (s, 3H):
MS (+ve ESI): 225 (M−H)$^+$.

c) 4-iodoaniline (4.89 g, 22.3 mmol) and 4-chloro-6,7-dimethoxyquinazoline (5.00 g, 22.3 mmol), in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded 4-(4-iodoanilino)-6,7-dimethoxyquinazoline (9.38 g, 95% yield) as a white solid:
$^1$H-NMR (DMSO d$_6$): 11.33 (s, 1H), 8.81 (s, 1H), 8.30 (s, 1H), 7.80 (s, 1H), 7.55 (d, 2H), 7.30 (s, 1H), 4.02 (s, 3H), 3.93 (s, 3H):
MS (−ve ESI): 406 (M−H)$^−$,
MS (+ve ESI): 408 (M+H)$^+$.

EXAMPLE 2

Preparation of Compound No. 2 in Table 1

Palladium (II) acetate (11 mg, 0.05 mmol) was added to a solution of 4-(4-iodophenoxy)-6,7-dimethoxyquinazoline (205 mg, 0.50 mmol), ethyl acrylate (50 mg, 0.50 mmol) and tri(o-tolyl)phosphine (30 mg, 0.10 mmol) in a mixture of triethylamine (3 ml) and acetonitrile (9 ml) and the reaction heated at reflux for 16 hours under an inert atmosphere. The reaction was cooled to ambient temperature, poured into water (30 ml), diluted with ethyl acetate (25 ml) and filtered through celite. The organic layer was separated, the aqueous was extracted with ethyl acetate (2×25 ml) and the combined organic layers were dried over magnesium sulphate before solvent evaporation in vacuo. Purification by flash chromatography on silica gel, eluting with ethyl acetate/isohexane (1:1), yielded 4-(4-(2-carboethoxy)ethenyl)phenoxy)-6,7-dimethoxyquinazoline (130 mg, 68% yield) as a cream solid:
$^1$H-NMR (DMSO d$_6$): 8.55 (s, 1H), 7.83 (d, 2H, J=8 Hz), 7.70 (d, 1H, J=19 Hz), 7.55 (s, 1H), 7.35 (d, 3H), 7.20 (s, 1H), 6.65 (d, 1H, J=19 Hz), 4.20 (q, 2H), 4.02 (s, 3H), 3.95 (s, 3H), 1.25 (t, 3H):
MS (+ve ESI): 381 (M+H)$^+$.

4-(4-Iodophenoxy)-6,7-dimethoxyquinazoline, used as the starting material, was obtained as follows:
A solution of 4-chloro-6,7-dimethoxyquinazoline (224 mg, 1.00 mmol), potassium carbonate (152 mg, 1.10 mmol) and 4-iodophenol (244 mg, 1.10 mmol) in dimethylformamide (4 ml) was heated at 110° C. for 2 hours before the reaction was allowed to cool to ambient temperature. The reaction was poured into water and the solid which had precipitated was collected by suction filtration and washed with a mixture of diethyl ether (10 ml), ethyl acetate (10 ml) and isohexane (10 ml). Drying of this material yielded, yielded 4-(4-iodophenoxy)-6,7-dimethoxyquinazoline (340 mg, 83% yield) as a white solid:
$^1$H-NMR (DMSO d$_6$): 8.55 (s, 1H), 7.80 (d, 2H, J=8 Hz), 7.50 (s, 1H), 7.35 (s, 1H), 7.15 (d, 2H, J=8 Hz), 3.95 (s, 3H), 3.90 (s, 3H):
MS (+ve ESI): 409 (M−H)$^+$.

EXAMPLE 3

Preparation of Compound No. 3 in Table 1

A mixture of 4-(4-(2-carboxy)ethenyl)anilino)-6,7-dimethoxyquinazoline (150 mg, 0.39 mmol), 4-(dimethylamino)pyridine (104 mg, 0.85 mmol), aniline (39 mg, 0.43 mmol) and 1-(3-dimethylaminopropyl)-3-ethylcarbodiimide hydrochloride (EDCI) (81 mg, 0.43 mmol) mmol) in dimethylacetamide (3.0 ml) was stirred at ambient temperature for 16 hours and then heated at 100° C. for 4 hours. The reaction was cooled, acidified by addition of 2.0N hydrochloric acid (7.0 ml, 14.0 mmol) and the precipitated solid collected by suction filtration. Drying in vacuo yielded the title compound (144 mg, 87% yield) as a white solid:
$^1$H-NMR (DMSO d$_6$): 11.42 (s, 1H), 11.30 (s, 1H), 8.85 (s, 1H), 8.30 (s, 1H), 7.80 (d, 2H), 7.70 (dd, 4H), 7.60 (d, 1H), 7.3 (t, 3H), 7.05 (t, 1H), 6.9 (d, 1H), 4.05 (s, 3H), 3.95(s, 3H):
MS (−ve ESI): 425 (M−H)$^−$,
MS (+ve ESI): 427 (M+H)$^+$.

4-(4-(2-carboxy)ethenyl)anilino)-6,7-dimethoxyquinazoline, used as the starting material, was obtained as follows:
a) Palladium (II) acetate (303 mg, 1.35 mmol) was added to a solution of 4-(4-iodoanilino)-6,7-dimethoxyquinazoline (see example 1c) (6.00 g, 13.5 mmol), ethyl acrylate (1.35 g, 13.5 mmol) and tri(o-tolyl)phosphine (821 mg, 2.70 mmol) in a mixture of triethylamine (60 ml) and acetonitrile (200 ml) and the reaction heated at reflux for 20 hours under an inert atmosphere. The reaction was cooled to ambient temperature, poured into water (600 ml), diluted with ethyl acetate (200 ml) and filtered through celite. The organic layer was separated, the aqueous was extracted with ethyl acetate (2×200 ml) and the combined organic layers were dried over magnesium sulphate before solvent evaporation in vacuo. Purification by flash chromatography on silica gel, eluting with ethyl acetate, yielded 4-(4-(2-carboethoxy)ethenyl)anilino)-6,7-dimethoxyquinazoline (4.36 g, 85% yield) as a yellow solid:
$^1$H-NMR (DMSO d$_6$): 9.6 (s, 1H), 8.5 (s, 1H), 7.9 (d, 2H), 7.85 (s, 1H), 7.75 (d, 2H), 7.65 (d, 1H), 7.2 (s, 1H), 6.5 (d, 1H), 4.2 (q, 2H), 4.0 (s, 3H), 3.9 (s, 3H), 1.25 (t, 3H):
MS (−ve ESI): 378 (M−H)$^−$,
MS (+ve ESI): 380 (M+H)$^+$.

b) Aqueous sodium hydroxide solution (3.3N, 20.0 ml, 66.3 mmol) was added to a solution of 4-(4-(2-carboethoxy)ethenyl)anilino)-6,7-dimethoxyquinazoline (8.38 g, 22.1 mmol) in ethanol (200 ml) and the reaction was heated at reflux for 16 hours. The reaction was allowed to cool to ambient temperature, diethyl ether (200 ml) was added and the solid material collected by suction filtration. The solid was taken up in ethanol (200 ml), acidified by addition of 1.0N hydrochloric acid (100 ml, 100 mmol) and the solid collected by suction filtration. Drying in vacuo yielded 4-(4-(2-carboxy)ethenyl)anilino)-6,7-dimethoxyquinazoline (8.25 g, 97% yield) as a yellow solid:
$^1$H-NMR (DMSO d$_6$): 10.73 (s, 1H), 8.65 (s, 1H), 8.25 (s, 1H), 7.95 (d, 2H), 7.70 (d, 2H), 7.55 (d, 1H), 7.30 (s, 1H), 7.30 (s, 1H), 6.45 (d, 1H), 4.00 (s, 3H), 3.90 (s, 3H):
MS (−ve ESI): 350 (M−H)$^−$,
MS (+ve ESI): 352 (M+H)$^+$.

c) As an alternative, a solution of 4-aminocinnamic acid (199 mg, 1.00 mmol) and 4-chloro-6,7-dimethoxyquinazoline (224 mg, 1.00 mmol) in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded 4-(4-(2-carboxy)ethenyl)anilino)-6,7-dimethoxyquinazoline (350 mg, 90% yield) as a yellow solid.

EXAMPLE 4

Preparation of Compound No. 4 in Table 1

An analogous reaction to that described in example 3, but starting with ethylamine hydrochloride (35 mg, 0.43 mmol)

(in place of the aniline), yielded the title compound (109 mg, 74% yield) as a pale-yellow solid:

$^1$H-NMR (DMSO d$_6$): 9.50 (s, 1H), 8.50 (s, 1H), 7.91–8.00 (m, 3H), 7.85 (s, 1H), 7.50–7.60 (m, 2H), 7.40 (d, 1H), 7.20 (s, 1H), 6.50 (d, 1H), 4.00 (s, 3H), 3.98 (s, 3H), 3.50–3.80 (m, 8H), 3.30 (m, 2H), 1.05 (m, 3H):

MS (−ve ESI): 377 (M−H)$^-$,
MS (+ve ESI): 379 (M+H)$^+$.

EXAMPLE 5

Preparation of Compound No. 5 in Table 1

An analogous reaction to that described in example 3, but starting with morpholine (37 mg, 0.43 mmol), yielded the title compound (125 mg, 77% yield) as a white solid:

$^1$H-NMR (DMSO d$_6$): 11.17 (s, 1H), 8.80 (s, 1H), 8.25 (s, 1H), 7.80 (s, 4H), 7.50 (d, 1H), 7.30 (s, 1H), 7.20 (s, 1H), 4.00 (s, 3H), 3.95 (s, 3H), 3.50–3.80 (m, 8H):

MS (−ve ESI): 419 (M−H)$^-$.

EXAMPLE 6

Preparation of Compound No. 6 in Table 1

A solution of 1-(3-dimethylaminopropyl)-3-ethylcarbodiimide hydrochloride (EDCI) (63 mg, 0.33 mmol) and 4-(dimethylamino)pyridine (73 mg, 0.60 mmol) in dimethylacetamide (3.0 ml) was added to 4-methylaniline (35 mg, 0.33 mmol) and 4-(4-(2-carboxy)ethenyl)anilino)-6,7-dimethoxyquinazoline (116 mg, 0.30 mmol). The reaction was stirred at ambient temperature for 48 hours and then heated at 100° C. for 4 hours before being cooled to ambient temperature. Brine (10 ml) was added and the reaction allowed to stand for 16 hours before the solid was collected by suction filtration (analogous reactions which failed to yield a solid precipitate were extracted with dichloromethane (2×5 ml) and the dichloromethane layer evaporated in vacuo to give a solid product). Drying in vacuo yielded the title compound (77.4 mg, 59% yield) as a white solid:

$^1$H-NMR (DMSO d$_6$): 10.10 (s, 1H), 9.65 (s, 1H), 8.65 (s, 1H), 8.00 (d, 2H), 7.90 (s, 1H), 7.70 (d, 2H), 7.65 (d, 2H), 7.55 (d, 1H); 7.25 (s, 1H), 7.15 (d, 2H), 6.80 (d, 1H), 4.02 (s, 3H), 3.95 (s, 3H), 2.30 (s, 3H):

MS (+ve ESI): 441 (M+H)$^+$.

EXAMPLE 7

Preparation of Compound No. 7 in Table 1

An analogous reaction to that described in example 6, but starting with 1,3-dimethylbutylamine (33 mg, 0.33 mmol) yielded the title compound (97.2 mg, 75% yield) as a white solid:

$^1$H-NMR (DMSO d$_6$): 9.65 (s, 1H), 8.65 (s, 1H), 7.90–7.95 (m, 3H), 7.85 (d, 1H), 7.60 (d, 2H), 7.40 (d, 1H), 7.25 (s, 1H), 6.55 (d, 1H), 4.02 (s, 4H), 3.95 (s, 3H), 1.60–1.70 (m, 1H), 1.40–1.50 (m, 1H), 1.20–1.30 (m, 1H), 1.10 (d, 3H), 0.85–0.90 (m, 6H):

MS (+ve ESI): 435 (M+H)$^+$.

EXAMPLE 8

Preparation of Compound No. 8 in Table 1

An analogous reaction to that described in example 6, but starting with 2-chlorobenzylamine (47 mg, 0.33 mmol) yielded the title compound (97.1 mg, 68% yield) as a white solid:

$^1$H-NMR (DMSO d$_6$): 9.70 (s, 1H), 8.60–8.65 (m, 1H), 8.55 (s, 1H), 7.95 (d, 2H), 7.90 (s, 1H), 7.60 (d, 2H), 7.45–7.50 (m, 2H), 7.30–7.42 (m, 3H), 7.25 (s, 1H), 6.70 (d, 1H), 4.50 (d, 2H), 4.02 (s, 3H), 3.95 (s, 3H):

MS (+ve ESI): 475 (M+H)$^+$.

EXAMPLE 9

Preparation of Compound No. 9 in Table 1

An analogous reaction to that described in example 6, but starting with 3-amino-1,2-propanediol (30 mg, 0.33 mmol) yielded the title compound (72.7 mg, 57% yield) as a white solid:

$^1$H-NMR (DMSO d$_6$): 9.62 (s, 1H), 8.55 (s, 1H), 8.10–8.05 (m, 1H), 7.95 (d, 2H), 7.90 (s, 1H), 7.60 (d, 2H), 7.45 (d, 2H), 7.25 (s, 1H), 6.70 (d, 1H), 4.85 (d, 1H), 4.60 (t, 1H), 4.02 (s, 3H), 3.95 (s, 3H), 3.40–3.30 (m, 4H):

MS (+ve ESI): 425 (M+H)$^+$.

EXAMPLE 10

Preparation of Compound No. 10 in Table 1

An analogous reaction to that described in example 6, but starting with isobutylamine (24 mg, 0.33 mmol) yielded the title compound (87.5 mg, 72% yield) as a white solid:

$^1$H-NMR (DMSO d$_6$): 9.62 (s, 1H), 8.55 (s, 1H), 8.05–8.10 (m, 1H), 7.95 (d, 2H), 7.90 (s, 1H), 7.60 (d, 2H), 7.45 (d, 1H), 7.25 (s, 1H), 6.65 (d, 1H), 4.02 (s, 3H), 3.95 (s, 3H), 3.00–3.10 (m, 2H), 1.70–1.80 (m, 1H), 0.92 (s, 3H), 0.88 (s, 3H):

MS (+ve ESI): 407 (M+H)$^+$.

EXAMPLE 11

Preparation of Compound No. 11 in Table 1

An analogous reaction to that described in example 6, but starting with 2-methyl-1-amylamine (33 mg, 0.33 mmol) yielded the title compound (88.4 mg, 75% yield) as a white solid:

$^1$H-NMR (DMSO d$_6$): 9.65 (s, 1H), 8.55 (s, 1H), 8.00–8.05 (m, 1H), 7.97 (d, 2H), 7.95 (s, 1H), 7.60 (d, 2H), 7.45 (d, 1H), 7.25 (s, 1H), 6.65 (d, 1H), 4.00 (s, 3H), 3.95 (s, 3H), 3.10–3.20 (m, 1H), 2.95–3.07 (m, 1H), 1.60–1.70 (m, 1H), 1.20–1.40 (m, 3H), 1.05–1.15 (m, 1H), 0.85–0.90 (m, 6H):

MS (+ve ESI): 435 (M+H)$^+$.

EXAMPLE 12

Preparation of Compound No. 12 in Table 1

An analogous reaction to that described in example 6, but starting with 2-methoxyethylamine (25 mg, 0.33 mmol) yielded the title compound (87 mg, 71% yield) as a white solid:

$^1$H-NMR (DMSO d$_6$): 9.68 (s, 1H), 8.55 (s, 1H), 8.10–8.20 (m, 1H), 7.95 (d, 2H), 7.90 (s, 1H), 7.60 (d, 2H), 7.45 (d, 1H), 7.25 (s, 1H), 6.65 (d, 1H), 4.00 (s, 3H), 3.95 (s, 3H), 3.35–3.50 (m, 4H), 3.30 (s, 3H):

MS (+ve ESI): 409 (M+H)$^+$.

EXAMPLE 13

Preparation of Compound No. 13 in Table 1

An analogous reaction to that described in example 6, but starting with propargylamine (18 mg, 0.33 mmol) yielded the title compound (8.4 mg, 7% yield) as a white solid:
$^1$H-NMR (DMSO d$_6$): 9.60 (s, 1H), 8.52 (s, 1H), 8.45–8.50 (m, 1H), 7.95 (d, 2H), 7.90 (s, 1H), 7.62 (d, 2H), 7.50 (d, 1H), 7.25 (s, 1H), 6.70 (d, 1H), 4.00–4.05 (m, 2H), 3.98 (s, 3H), 3.95 (s, 3H), 3.15 (s, 1H):
MS (+ve ESI): 389 (M+H)$^+$.

EXAMPLE 14

Preparation of Compound No. 14 in Table 1

An analogous reaction to that described in example 6, but starting with 3-(dimethylamino)-n-propylamine (34 mg, 0.33 mmol) yielded the title compound (58.7 mg, 45% yield) as a white solid:
$^1$H-NMR (DMSO d$_6$): 9.60 (s, 1H), 8.55 (s, 1H), 8.05 (t, 1H), 7.96 (d, 2H), 7.88 (s, 1H), 7.60 (d, 2H), 7.40 (d, 1H), 7.25 (s, 1H), 6.70 (d, 1H), 4.00 (s, 3H), 3.95 (s, 3H), 3.20–3.25 (m, 2H), 2.20–2.30 (m, 2H), 2.15 (s, 6H), 1.55–1.65 (m, 2H):
MS (+ve ESI): 436 (M+H)$^+$.

EXAMPLE 15

Preparation of Compound No. 15 in Table 1

An analogous reaction to that described in example 6, but starting with n-butylamine (24 mg, 0.33 mmol) yielded the title compound (96.4 mg, 79% yield) as a white solid:
$^1$H-NMR (DMSO d$_6$): 9.65 (s, 1H), 8.52 (s, 1H), 8.05 (t, 1H), 7.95 (s, 1H), 7.92 (d, 2H), 7.60 (d, 2H), 7.42 (d, 1H), 7.23 (s, 1H), 6.70 (d, 1H), 4.00 (s, 3H), 3.95 (s, 3H), 3.15–3.25 (m, 2H), 1.42–1.52 (m, 2H), 1.30–1.38 (m, 2H), 0.90–0.95 (m, 3H):
MS (+ve ESI): 407 (M+H)$^+$.

EXAMPLE 16

Preparation of Compound No. 16 in Table 1

An analogous reaction to that described in example 6, but starting with 2-amino-1-methoxypropane (29 mg, 0.33 mmol) yielded the title compound (52.6 mg, 42% yield) as a white solid:
$^1$H-NMR (DMSO d$_6$): 9.70 (s, 1H), 8.55 (s, 1H), 8.00–7.95 (m, 3H), 7.95 (s, 1H), 7.60 (d, 2H), 7.40 (d, 1H), 7.21 (s, 1H), 6.70 (d, 1H), 4.02–4.12 (m, 1H), 4.00 (s, 3H), 3.98 (s, 3H), 3.22–3.40 (m, 5H), 1.11 (d, 3H):
MS (+ve ESI): 423 (M+H)$^+$.

EXAMPLE 17

Preparation of Compound No. 17 in Table 1

An analogous reaction to that described in example 6, but starting with 3-methylaniline (35 mg, 0.33 mmol) yielded the title compound (88.8 mg, 67% yield) as a white solid:
$^1$H-NMR (DMSO d$_6$): 10.10 (s, 1H), 9.65 (s, 1H), 8.55 (s, 1H), 8.00 (d, 2H), 7.90 (s, 1H), 7.67 (d, 2H), 7.60 (s, 1H), 7.50–7.55 (m, 2H), 7.20–7.30 (m, 2H), 6.90–6.95 (m, 1H), 6.80 (d, 1H), 4.02 (s, 3H), 3.95 (s, 3H), 2.35 (s, 3H):
MS (+ve ESI): 441 (M+H)$^+$.

EXAMPLE 18

Preparation of Compound No. 18 in Table 1

An analogous reaction to that described in example 6, but starting with 3-methylcyclohexylamine (37 mg, 0.33 mmol) yielded the title compound (111 mg, 83% yield) as a white solid:
$^1$H-NMR (DMSO d$_6$): 9.60 (s, 1H), 8.51 (s, 1H), 7.84–7.96 (m, 4H), 7.57 (d, 2H, J=8 Hz), 7.40 (d, 1H, J=16 Hz), 7.21 (s, 1H), 6.55 (d, 1H, J=16 Hz), 4.00 (s, 3H), 3.96 (s, 3H), 3.65 (m, 1H), 1.40–1.84 (m, 7H), 1.20–1.37 (m, 1H), 1.00–1.15 (m, 1H), 0.93 (d, 3H, J=7 Hz), 0.77–0.91 (m, 1H):
MS (+ve ESI): 447 (M+H)$^+$.

EXAMPLE 19

Preparation of Compound No. 19 in Table 1

An analogous reaction to that described in example 6, but starting with 2-aminoindan hydrochloride (44 mg, 0.33 mmol) yielded the title compound (117.8 mg, 84% yield) as a white solid:
$^1$H-NMR (DMSO d$_6$): 9.75 (s, 1H), 8.50 (s, 1H), 8.40 (d, 1H), 7.90–8.00 (m, 3H), 7.60 (d, 2H), 7.45 (d, 1H), 7.25–7.30 (m, 2H), 7.20 (s, 1H), 7.10–7.15 (m, 2H), 6.60 (d, 1H), 4.65–4.75 (m, 1H), 4.02 (s, 3H), 3.95 (s, 3H), 3.20–3.30 (m, 2H), 2.80–2.90 (m, 2H):
MS (+ve ESI): 467 (M+H)$^+$.

EXAMPLE 20

Preparation of Compound No. 20 in Table 1

An analogous reaction to that described in example 6, but starting with 4-chlorotetrahydro-3-thiopheneamine-1,1-dioxide hydrochloride (55 mg, 0.33 mmol) yielded the title compound (88.2 mg, 58% yield) as a white solid:
$^1$H-NMR (DMSO d$_6$): 9.61 (s, 1H), 8.77 (d, 1H, J=6 Hz), 8.52 (s, 1H), 7.94 (d, 2H, J=8 Hz), 7.87 (s, 1H), 7.62 (d, 2H, J=8 Hz), 7.50 (d, 1H, J=16 Hz), 7.21–7.28 (m, 2H), 7.25 (s, 1H), 6.91 (m, 1H), 6.57 (d, 1H, J=16 Hz), 5.27–5.33 (m, 1H), 4.00 (s, 3H), 3.97 (s, 3H), 3.78 (dd, 1H, J=5,8 Hz), 3.11 (dd, 1H, J=5,8 Hz):
MS (+ve ESI): 504 (M+H)$^+$.

EXAMPLE 21

Preparation of Compound No. 21 in Table 1

An analogous reaction to that described in example 6, but starting with 5-methyl-2-(aminomethyl)furan (37 mg, 0.33 mmol) yielded the title compound (99.2 mg, 74% yield) as a white solid:
$^1$H-NMR (DMSO d$_6$): 9.60 (s, 1H), 8.55 (s, 1H), 8.55 (t, 1H), 7.90 (d, 2H), 7.88 (s, 1H), 7.60 (d, 2H), 7.45 (d, 1H), 7.25 (s, 1H), 6.63 (d, 1H), 6.20 (d, 1H), 6.00 (d, 1H), 4.35 (d, 2H), 4.02 (s, 3H), 3.95 (s, 3H), 2.25 (s, 3H):
MS (+ve ESI): 445 (M+H)$^+$.

EXAMPLE 22

Preparation of Compound No. 22 in Table 1

An analogous reaction to that described in example 6, but starting with cyclopropylamine (18 mg, 0.33 mmol) yielded the title compound (79.4 mg, 68% yield) as a white solid:
$^1$H-NMR (DMSO d$_6$): 9.60 (s, 1H), 8.55 (s, 1H), 8.15 (d, 1H), 7.95 (d, 2H), 7.90 (s, 1H), 7.60 (d, 2H), 7.40 (d, 1H), 7.22 (s, 1H), 6.55 (d, 1H), 4.02 (s, 3H), 3.95 (s, 3H), 2.80–2.90 (m, 1H), 0.70–0.75 (m, 2H), 0.50–0.55 (m, 2H):
MS (+ve ESI): 391 (M+H)$^+$.

EXAMPLE 23

Preparation of Compound No. 23 in Table 1

An analogous reaction to that described in example 6, but starting with cyclobutylamine (23 mg, 0.33 mmol) yielded the title compound (81.6 mg, 67% yield) as a white solid:
$^1$H-NMR (DMSO d$_6$): 9.58 (s, 1H), 8.50 (s, 1H), 8.30 (d, 1H), 7.95 (d, 2H), 7.90 (s, 1H), 7.60 (d, 2H), 7.40 (d, 1H), 7.22 (s, 1H), 6.55 (d, 1H), 4.30–4.40 (m, 1H), 4.02 (s, 3H), 3.95 (s, 3H), 2.20–2.30 (m, 2H), 1.90–2.00 (m, 2H), 1.65–1.75 (m, 2H):
MS (+ve ESI): 405 (M+H)$^+$.

EXAMPLE 24

Preparation of Compound No. 24 in Table 1

An analogous reaction to that described in example 6, but starting with cyclopentylamine (28 mg, 0.33 mmol) yielded the title compound (81.6 mg, 65% yield) as a white solid:
$^1$H-NMR (DMSO d$_6$): 9.60 (s, 1H), 8.55 (s, 1H), 8.00 (d, 1H), 7.92 (d, 2H), 7.90 (s, 1H), 7.60 (d, 2H), 7.40 (d, 1H), 7.22 (s, 1H), 6.55 (d, 1H), 4.10–4.20 (m, 1H), 4.02 (s, 3H), 3.95 (s, 3H), 1.85–1.95 (m, 2H), 1.75–1.85 (m, 2H), 1.50–1.60 (m, 2H), 1.40–1.50 (m, 2H):
MS (+ve ESI): 419 (M+H)$^+$.

EXAMPLE 25

Preparation of Compound No. 25 in Table 1

An analogous reaction to that described in example 6, but starting with cyclohexylamine (36 mg, 0.33 mmol) yielded the title compound (94.7 mg, 73% yield) as a white solid:
$^1$H-NMR (DMSO d$_6$): 9.60 (s, 1H), 8.55 (s, 1H), 7.93 (m, 3H), 7.90 (s, 1H), 7.60 (d, 2H), 7.40 (d, 1H), 7.22 (s, 1H), 6.60 (d, 1H), 4.02 (s, 3H), 3.95 (s, 3H), 3.55–3.70 (m, 1H), 1.78–1.85 (m, 2H), 1.65–1.75 (m, 2H), 1.50–1.60 (m, 1H), 1.15–1.40 (m, 5H):
MS (+ve ESI): 433 (M+H)$^+$.

EXAMPLE 26

Preparation of Compound No. 26 in Table 1

An analogous reaction to that described in example 6, but starting with piperidine (28 mg, 0.33 mmol) yielded the title compound (89.9 mg, 72% yield) as a white solid:
$^1$H-NMR (DMSO d$_6$): 9.55 (s, 1H), 8.50 (s, 1H), 7.90 (d, 2H), 7.85 (s, 1H), 7.70 (d, 2H), 7.45 (d, 1H, J=16 Hz), 7.20 (s, 1H), 7.15 (d, 1H, J=16 Hz), 3.98 (s, 3H), 3.93 (s, 3H), 3.65 (m, 2H), 3.55 (m, 2H), 1.63 (m, 2H), 1.50 (m, 4H):
MS (+ve ESI): 419 (M+H)$^+$.

EXAMPLE 27

Preparation of Compound No. 27 in Table 1

An analogous reaction to that described in example 6, but starting with 3-aminopyridine (31 mg, 0.33 mmol) yielded the title compound (41.5 mg, 32% yield) as a white solid:
$^1$H-NMR (DMSO d$_6$): 10.39 (s, 1H), 9.60 (s, 1H), 8.85 (m, 1H), 8.55 (s, 1H), 8.30 (m, 1H), 8.15 (m, 1H), 8.00 (d, 2H), 7.88 (s, 1H), 7.7 (d, 2H), 7.65 (d, 1H, J=16 Hz), 7.40 (m, 1H), 7.25 (s, 1H), 6.80 (d, 1H J=16 Hz), 3.99 (s, 3H), 3.95 (s, 3H):
MS (+ve ESI): 428 (M+H)$^+$.

EXAMPLE 28

Preparation of Compound No. 28 in Table 1

An analogous reaction to that described in example 6, but starting with 2-methoxyaniline (41 mg, 0.33 mmol) yielded the title compound (36.9 mg, 27% yield) as a white solid:
$^1$H-NMR (DMSO d$_6$): 9.65 (s, 1H), 9.28 (s, 1H), 8.55 (s, 1H), 8.20 (m, 1H), 7.95 (d, 2H), 7.90 (s, 1H), 7.65 (d, 2H), 7.55 (d, 1H, J=16 Hz), 7.23 (s, 1H), 7.13 (d, 1H, J=16 Hz), 7.08 (m, 2H), 6.95 (m, 1H), 4.0 (s, 3H), 3.98 (s, 3H), 3.9 (s, 3H):
MS (+ve ESI): 457 (M+H)$^+$.

EXAMPLE 29

Preparation of Compound No. 29 in Table 1

An analogous reaction to that described in example 6, but starting with 2-methylaniline (35 mg, 0.33 mmol) yielded the title compound (90.2 mg, 68% yield) as a white solid:
$^1$H-NMR (DMSO d$_6$): 9.65 (s, 1H), 9.50 (s, 1H), 8.55 (s, 1H), 7.95 (d, 2H), 7.88 (s, 1H), 7.68 (d, 2H), 7.60 (m, 1H), 7.55 (d, 1H, J=16 Hz), 7.20 (m, 3H), 7.10 (m, 1H), 6.95 (d, 1H, J=16 Hz), 4.00 (s, 3H), 3.95 (s, 3H), 2.30 (s, 3H):
MS (+ve ESI): 441 (M+H)$^+$.

EXAMPLE 30

Preparation of Compound No. 30 in Table 1

An analogous reaction to that described in example 6, but starting with 3-methoxyaniline (41 mg, 0.33 mmol) yielded the title compound (75.1 mg, 55% yield) as a white solid:
$^1$H-NMR (DMSO d$_6$): 10.15 (s, 1H), 9.65 (s, 1H), 8.55 (s, 1H), 7.95 (d, 2H), 7.90 (s, 1H), 7.65 (d, 2H), 7.60 (d, 1H, J=16 Hz), 7.43 (s, 1H), 7.20 (m, 3H), 6.78 (d, 1H, J=16 Hz), 6.65 (m, 1H), 4.00 (s, 3H), 3.98 (s, 3H), 3.78 (s, 3H):
MS (+ve ESI): 457 (M+H)$^+$.

EXAMPLE 31

Preparation of Compound No. 31 in Table 1

An analogous reaction to that described in example 6, but starting with 4-chloroaniline (42 mg, 0.33 mmol) yielded the title compound (76.7 mg, 56% yield) as a white solid:
$^1$H-NMR (DMSO d$_6$): 10.35 (s, 1H), 9.70 (s, 1H), 8.55 (s, 1H), 8.00 (d, 2H), 7.90 (s, 1H), 7.75 (d, 2H), 7.65 (d, 2H), 7.60 (d, 1H, J=16 Hz), 7.40 (d, 2H), 7.25 (s, 1H), 6.80 (d, 1H, J=16 Hz), 4.00 (s, 3H), 3.95 (s, 3H):
MS (+ve ESI): 461 (M+H)$^+$.

EXAMPLE 32

Preparation of Compound No. 32 in Table 1

A solution 4-chloro-6-methoxy-7-(3-morpholinopropoxy)quinazoline (6.90 g, 20.0 mmol) and 4-aminocinnamic acid hydrochloride (4.16 g, 20.8 mmol) in isopropanol (100 ml) was heated at reflux for 3 hours before the reaction was allowed to cool to ambient temperature. The solid which had precipitated was collected by suction filtration and washed with diethyl ether (2×50 ml). Drying of this material yielded the title compound (7.28 g, 68% yield) as a white solid:

$^1$H-NMR (DMSO d$_6$): 11.58 (s, 1H), 11.14 (s, 1H), 8.85 (s, 1H), 8.45 (s, 1H), 7.80 (dd, 4H), 7.60 (d, 1H, J=16 Hz), 7.45 (s, 1H), 6.55 (d, 1H, J=16 Hz), 4.30 (t, 2H), 4.05 (s, 3H), 3.95 (m, 2H), 3.80 (m, 2H), 3.50 (m, 2H), 3.30 (m, 2H), 3.10 (m, 2H), 2.30 (m, 2H):

MS (+ve ESI): 465 (M+H)$^+$.

4-Chloro-6-methoxy-7-(3-morpholinopropoxy)quinazoline, used as the starting material, was obtained as follows:

a) A mixture of morpholine (261 ml, 3.00 mol) and 1-bromo-3-chloropropane (148 ml, 1.50 mol) in toluene (900 ml) was stirred for 18 hours at ambient temperature. Additional 1-bromo-3-chloropropane (25 ml, 0.25 mol) was added, the reaction was stirred for a further 1 hour and then filtered to remove the precipitated solid before the filtrate was concentrated in vacuo. Distillation of the crude oil yielded b) N-(3-chloropropyl)-morpholine (119.3 g, 49% yield) as the fraction boiling at 70–80° C./2.6 mmHg:

$^1$H-NMR (DMSO d$_6$): 3.65 (t, 2H), 3.55 (m, 4H), 2.40 (t, 2H), 2.39 (m, 4H), 1.85 (m, 2H):

MS (+ve ESI): 164 (M+H)$^+$.

b) N-(3-Chloropropyl)morpholine (90 g, 0.55 mol) was added dropwise, over 30 minutes, to a solution of ethyl vanillate (98 g, 0.50 mol) and powdered potassium carbonate (104 g, 0.75 mol) in dimethylformamide (300 ml) at 80° C. The reaction was heated at 80° C. for 90 minutes, cooled to ambient temperature, filtered and the filtrate concentrated in vacuo. The crude product was taken up in diethyl ether (1000 ml), filtered and washed with water (2×200 ml) and brine (200 ml). Solvent evaporation in vacuo yielded ethyl 3-methoxy-4-(3-morpholinopropoxy)benzoate (161.5 g, 100% yield) as a pale yellow oil which crystallised on standing to afford a pale yellow solid:

$^1$H-NMR (DMSO d$_6$): 7.55 (dd, 1H), 7.40 (d, 1H), 7.05 (d, 1H), 4.30 (q, 2H), 4.05 (t, 2H), 3.80 (s, 3H), 3.55 (m, 4H), 2.40 (t, 2H), 2.35 (m, 4H), 1.90 (m, 2H), 1.30 (t, 3H):

MS (−ve ESI): 324 (M−H)$^-$.

c) Concentrated sulphuric acid (110 ml) and concentrated nitric acid (19.0 ml, 0.289 mol) were added cautiously, over a 50 minute period, to a two-phase system containing a stirred solution of ethyl 3-methoxy-4-(3-morpholinopropoxy)benzoate (76.5 g, 0.237 mol) in dichloromethane (600 ml), acetic acid (300 ml) and water (70 ml) at 5° C. The reaction was allowed to warm to ambient temperature over 18 hours, the aqueous phase was separated, and the aqueous phase was taken to pH 9 by addition of 40% aqueous sodium hydroxide solution (775 ml). Extraction of the aqueous phase with dichloromethane (3×600 ml) and subsequent solvent evaporation in vacuo yielded ethyl 3-methoxy-4-(3-morpholinopropoxy)-6-nitrobenzoate (141.3 g, 86% yield) as a yellow gum:

$^1$H-NMR (CDCl$_3$): 7.50 (s, 1H), 7.10 (s, 1H), 4.40 (q, 2H), 4.20 (t, 2H), 4.00 (s, 3H), 3.70 (m, 4H), 2.50 (t, 2H), 2.45 (m, 4H), 2.05 (m, 2H), 1.40 (t, 3H):

MS (+ve ESI): 369 (M+H)$^+$.

d) A suspension of ethyl 3-methoxy-4-(3-morpholinopropoxy)-6-nitrobenzoate (132.2 g, 359 mmol) and 10% palladium on carbon (3.0 g) in a mixture of ethanol (200 ml) and ethyl acetate (2000 ml) was stirred under an atmosphere of hydrogen for 18 hours. Removal of the catalyst by filtration, followed by solvent evaporation in vacuo yielded ethyl 3-methoxy-4-(3-morpholinopropoxy)-6-aminobenzoate (122 g, 100% yield) as a brown oil:

$^1$H-NMR (DMSO d$_6$): 7.15 (s, 1H), 6.40 (s, 2H), 6.35 (s, 1H), 4.20 (q, 2H), 3.95 (t, 2H), 3.65 (s, 3H), 3.55 (m, 4H), 2.40 (t, 2H), 2.35 (m, 4H), 1.85 (m, 2H), 1.25 (t, 3H):

MS (−ve ESI): 337 (M−H)$^-$,

MS (+ve ESI): 339 (M+H)$^+$.

e) A solution of ethyl 3-methoxy-4-(3-morpholinopropoxy)-6-aminobenzoate (130 g, 384 mmol) in formamide (280 ml) was heated at 180° C. for 3 hours, during which time a small amount (25 ml) of liquid distilled out of the reaction. The reaction was cooled to 125° C. and the excess formamide was evaporated in vacuo. Trituration of the solid residue with isopropanol (100 ml), followed by drying in vacuo, yielded 6-methoxy-7-(3-morpholinopropoxy)-3,4-dihydroquinazolin-4-one (83.0 g, 68% yield) as a pale brown solid:

$^1$H-NMR (DMSO d$_6$): 12.0 (s, 1H), 7.95 (s, 1H), 7.45 (s, 1H), 7.10 (s, 1H), 4.15 (t, 2H), 3.85 (s, 3H), 3.60 (m, 4H), 2.45 (t, 2H), 2.35 (m, 4H), 1.90 (m, 2H):

MS (−ve ESI): 318 (M−H)$^-$,

MS (+ve ESI): 320 (M+H)$^+$.

f) Dimethylformamide (2.0 ml) was added dropwise to a solution of 6-methoxy-7-(3-morpholinopropoxy)-3,4-dihydro-quinazolin-4-one (83.0 g, 261 mmol) in thionyl chloride (700 ml) and the reaction was heated at reflux for 3.5 hours. The reaction was cooled, excess thionyl chloride was removed in vacuo, the residue was taken up in water (500 ml) and this aqueous solution was taken to pH 9 by addition of saturated aqueous sodium bicarbonate solution (300 ml). The aqueous phase was extracted with dichloromethane (2×400 ml), the organic solution was washed with brine (400 ml) and the solvents were removed in vacuo. Trituration of the solid residue with ethyl acetate (150 ml), followed by drying in vacuo, yielded 4-chloro-6-methoxy-7-(3-morpholinopropoxy)quinazoline (53 g, 60% yield) as a pale brown solid:

$^1$H-NMR (CDCl$_3$): 8.85 (s, 1H), 7.39 (s, 1H), 7.38 (s, 1H), 4.30 (t, 2H), 4.05 (s, 3H), 3.70 (m, 4H), 2.60 (t, 2H), 2.50 (m, 4H), 2.10 (m, 2H):

MS (+ve ESI): 338 (M+H)$^+$.

EXAMPLE 33

Preparation of Compound No. 33 in Table 1

O-(7-Azabenzotriazol-1-yl)-N,N,N',N'-tetramethyluronium hexafluoro-phosphate (HATU) (192 mg, 0.50 mmol) was added to a suspension 4-(4-(2-carboxyethenyl)anilino)-6-methoxy-7-(3-mopholinopropoxy)quinazoline (232 mg, 0.50 mmol) in dimethylformamide (4.5 ml). After 5 minutes, cyclohexylmethylamine (56.9 mg, 0.50 mmol) was added and the reaction heated at 50° C. for 16 hours. The reaction was cooled, poured into water (10 ml) and diethyl ether (5 ml) was added. The solid which precipitated was collected by suction filtration and washed with water (10 ml) and diethyl ether (10 ml). Drying of the solid in vacuo yielded the title compound (149.9 mg, 59% yield) as a white solid:

$^1$H-NMR (DMSO d$_6$): 9.55 (s, 1H), 8.45 (s, 1H), 8.00 (t, 1H), 7.90 (d, 2H), 7.85 (s, 1H), 7.65 (d, 2H), 7.40 (d, 1H, J=16 Hz), 7.20 (s, 1H), 6.60 (d, 1H, J=16 Hz), 4.20 (t, 2H), 4.00 (s, 3H), 3.60 (m, 4H), 3.05 (m, 2H), 2.45 (t, 2H), 2.40 (m, 4H), 1.95 (t, 2H), 1.70 (m, 4H), 1.20 (m, 4H), 0.90 (m, 2H):

MS (+ve ESI): 560 (M+H)$^+$.

EXAMPLE 34

Preparation of Compound No. 34 in Table 1

An analogous reaction to that described in example 33, but starting with 5-amino-2-chloropyridine (64.6 mg, 0.50 mmol) yielded the title compound (188.2 mg, 72% yield) as a white solid:

$^1$H-NMR (DMSO d$_6$): 10.51 (s, 1H), 9.60 (s, 1H), 8.70 (d, 1H), 8.80 (s, 1H), 8.20 (dd, 1H), 7.95 (d, 2H), 7.85 (s, 1H), 7.65 (d, 2H), 7.65 (d, 1H, J=16 Hz), 7.50 (d, 1H), 7.20 (s, 1H), 6.75 (d, 1H, J=16 Hz), 4.20 (t, 2H), 3.99 (s, 3H), 3.60 (m, 4H), 2.45 (t, 2H), 2.40 (m, 4H), 1.95 (m, 2H):

MS (+ve ESI): 575 (M+H)$^+$.

EXAMPLE 35

Preparation of Compound No. 35 in Table 1

An analogous reaction to that described in example 33, but starting with furfurylamine (48.8 mg, 0.50 mmol) yielded the title compound (200 mg, 81% yield) as a white solid:

$^1$H-NMR (DMSO d$_6$): 9.55 (s, 1H), 8.45 (m, 2H), 7.9 (d, 2H), 7.85 (s, 1H), 7.60 (m, 3H), 7.45 (d, 1H, J=16 Hz), 7.20 (s, 1H), 6.60 (d, 1H, J=16 Hz), 6.40 (m, 1H), 6.25 (m, 1H), 4.40 (d, 2H), 4.20 (t, 2H), 3.99 (d, 3H), 3.60 (m, 4H), 2.45 (t, 2H), 2.40 (m, 4H), 1.95 (m, 2H):

MS (+ve ESI): 544 (M+H)$^+$.

EXAMPLE 36

Preparation of Compound No. 36 in Table 1

An analogous reaction to that described in example 33, but starting with tetrahydrofurfurylamine (50.8 mg, 0.50 mmol) yielded the title compound (61.6 mg, 25% yield) as a white solid:

$^1$H-NMR (DMSO d$_6$): 9.60 (s, 1H), 8.50 (s, 1H), 8.05 (t, 1H), 7.90 (d, 2H), 8.85 (s, 1H), 7.59 (d, 2H), 7.40 (d, 1H, J=16 Hz), 7.20 (s, 1H), 6.60 (d, 1H, J=16 Hz), 4.20 (t, 2H), 3.99 (s, 3H), 3.90 (m, 1H), 3.80 (m, 1H), 3.60 (m, 1H), 3.59 (m, 4H), 3.25 (m, 2H), 2.45 (t, 2H), 2.40 (m, 4H), 1.95 (m, 2H), 1.80 (m, 2H), 1.60 (m, 2H):

MS (+ve ESI): 541 (M+H)$^+$.

EXAMPLE 37

Preparation of Compound No. 37 in Table 1

An analogous reaction to that described in example 33, but starting with 2-aminopyridine (47.3 mg, 0.50 mmol) yielded the title compound (42.4 mg, 17% yield) as a white solid:

$^1$H-NMR (DMSO d$_6$): 10.60 (s, 1H), 9.60 (s, 1H), 8.50 (s, 1H), 8.30 (m, 1H), 8.25 (d, 1H), 7.95 (d, 2H), 7.80 (m, 2H), 7.60 (m, 3H), 7.20 (s, 1H), 7.10 (m, 1H), 6.99 (d, 1H, J=16 Hz), 4.20 (t, 2H), 3.99 (s, 3H), 3.60 (m, 4H), 2.45 (t, 2H), 2.40 (m, 4H), 1.99 (m, 2H):

MS (+ve ESI): 541 (M+H)$^+$.

EXAMPLE 38

Preparation of Compound No. 38 in Table 1

An analogous reaction to that described in example 33, but starting with 3-aminopyridine (47.3 mg, 0.50 mmol) yielded the title compound (138.9 mg, 57% yield) as a white solid:

$^1$H-NMR (DMSO d$_6$): 10.35 (s, 1H), 9.60 (s, 1H), 8.85 (m, 1H), 8.50 (s, 1H), 8.25 (d, 1H), 8.15 (dd, 1H), 7.99 (d, 2H), 7.85 (s, 1H), 7.65 (d, 2H), 7.60 (d, 1H, J=16 Hz), 7.40 (m, 1H), 6.80 (d, 1H, J=16 Hz), 4.20 (t, 2H), 3.99 (s, 3H), 3.60 (m, 4H), 2.45 (t, 2H), 2.40 (m, 4H), 1.99 (m, 2H):

MS (+ve ESI): 541 (M+H)$^+$.

EXAMPLE 39

Preparation of Compound No. 39 in Table 1

An analogous reaction to that described in example 33, but starting with 2-aminotoluene (53.9 mg, 0.50 mmol) yielded the title compound (239 mg, 95% yield) as a white solid:

$^1$H-NMR (DMSO d$_6$): 9.60 (s, 1H), 9.40 (s, 1H), 8.50 (s, 1H), 8.95 (d, 2H), 8.85 (s, 1H), 7.60 (m, 4H), 7.20 (m, 3H), 7.05 (m, 1H), 6.90 (d, 1H, J=16 Hz), 4.20 (t, 2H), 3.99 (s, 3H), 3.60 (m, 4H), 2.45 (t, 2H), 2.40 (m, 4H), 2.25 (s, 3H), 1.99 (m, 2H):

MS (+ve ESI): 554 (M+H)$^+$.

EXAMPLE 40

Preparation of Compound No. 40 in Table 1

An analogous reaction to that described in example 33, but starting with 1,3-dimethylbutylamine (50.9 mg, 0.50 mmol) yielded the title compound (61.8 mg, 25% yield) as a white solid:

$^1$H-NMR (DMSO d$_6$): 9.55 (s, 1H), 8.50 (s, 1H), 7.90 (d, 2H), 7.85 (s, 1H), 7.80 (m, 1H), 7.59 (d, 2H), 7.40 (d, 1H, J=16 Hz), 7.20 (s, 1H), 6.50 (d, 1H, J=16 Hz), 4.20 (t, 2H), 3.99 (s, 3H), 3.99 (m, 1H), 3.60 (m, 4H), 2.45 (t, 2H), 2.40 (m, 4H), 1.95 (m, 2H), 1.60 (m, 1H), 1.40 (m, 1H), 1.20 (m, 1H), 1.05 (d, 3H), 0.85 (d, 6H):

MS (+ve ESI): 548 (M+H)$^+$.

EXAMPLE 41

Preparation of Compound No. 41 in Table 1

An analogous reaction to that described in example 33, but starting with 2,2,2-trifluoroethylamine hydrochloride (67.8 mg, 0.50 mmol) yielded the title compound (7.8 mg, 3% yield) as a white solid:

$^1$H-NMR (DMSO d$_6$): 9.59 (s, 1H), 8.65 (t, 1H), 8.50 (s, 1H), 7.90 (d, 2H), 7.85 (s, 1H), 7.60 (d, 2H), 7.50 (d, 1H, J=16 Hz), 7.20 (s, 1H), 6.60 (d, 1H, J=16 Hz), 4.20 (t, 2H), 4.05 (m, 2H), 3.99 (s, 3H), 3.60 (m, 4H), 2.45 (t, 2H), 2.40 (m, 4H), 1.99 (m, 2H):

MS (+ve ESI): 546 (M+H)$^+$.

EXAMPLE 42

Preparation of Compound No. 42 in Table 1

An analogous reaction to that described in example 33, but starting with isobutylamine (36.8 mg, 0.50 mmol) yielded the title compound (39.1 mg, 17% yield) as a white solid:

$^1$H-NMR (DMSO d$_6$): 9.52 (s, 1H), 8.50 (s, 1H), 7.95 (m, 1H), 7.90 (d, 2H), 7.85 (s, 1H), 7.58 (d, 2H), 7.38 (d, 1H, J=16 Hz), 7.20 (s, 1H), 6.60 (d, 1H, J=16 Hz), 4.18 (t, 2H), 3.97 (s, 3H), 3.58 (m, 4H), 3.00 (t, 2H), 2.48 (t, 2H), 2.35 (m, 4H), 1.95 (m, 2H), 1.75 (m, 1H), 0.89 (d, 6H):

MS (+ve ESI): 520 (M+H)$^+$.

EXAMPLE 43

Preparation of Compound No. 43 in Table 1

An analogous reaction to that described in example 33, but starting with 2-methylpentylamine (50.9 mg, 0.50 mmol) yielded the title compound (33.5 mg, 13% yield) as a white solid:

$^1$H-NMR (DMSO d$_6$): 9.54 (s, 1H), 8.49 (s, 1H), 7.98 (t, 1H), 7.90 (d, 2H), 7.84 (s, 1H), 7.56 (d, 2H), 7.39 (d, 1H), 7.19 (s, 1H), 6.59 (d, 1H), 4.18 (d, 2H), 3.96 (s, 3H) 3.53–3.61 (m, 4H), 2.93–3.16 (m, 2H), 2.45 (t, 2H), 2.32–2.41 (m, 4H), 1.87–2.02 (m, 2H), 0.95–1.68 (m, 5H), 0.85 (t, 3H), 0.84 (d, 3H):

MS (+ve ESI): 548 (M+H)$^+$.

EXAMPLE 44

Preparation of Compound No. 44 in Table 1

An analogous reaction to that described in example 3c, but starting with 4-chloro-6-methoxy-7-benzyloxyquinazoline (150 mg, 0.50 mmol) and ethyl 4-aminocinnamate (96 mg, 0.50 mmol), yielded the title compound (226 mg, 92% yield) as an off-white solid:

$^1$H-NMR (DMSO d$_6$): 11.25 (s, 1H), 8.83 (s, 1H), 8.28 (s, 1H), 7.81 (m, 4H), 7.66 (d, 1H, J=15 Hz), 7.5 (d, 2H), 7.38–7.45 (m, 4H), 6.63 (d, 1H, J=16 Hz), 5.34 (s, 2H), 4.21 (q, 2H), 4.02 (s, 3H), 1.26 (t, 3H):

MS (+ve ESI): 456 (M+H)$^+$.

4-Chloro-6-methoxy-7-benzyloxyquinazoline, used as the starting material, was obtained as follows:

a) A mixture of 2-amino-4-benzyloxy-5-methoxybenzamide (10 g, 0.04 mol), (prepared according to *J. Med. Chem.* 1977, 20, 146–149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid yielded 7-benzyloxy-6-methoxy-3,4-dihydroquinazolin-4-one (8.7 g, 84% yield) as a white solid.

b) Dimethylformamide (0.2 ml) was added dropwise to a solution of 6-methoxy-7-benzyloxy-3,4-dihydroquinazolin-4-one (5.00 g, 17.9 mmol) in thionyl chloride (100 ml) and the reaction was heated at reflux for 1 hour. The reaction was cooled, excess thionyl chloride was removed in vacuo and the residue was azeotroped with toluene (3×50 ml) to remove the last of the thionyl chloride. The residue was taken up in dichloromethane (550 ml), the solution was washed with saturated aqueous sodium hydrogen carbonate solution (100 ml) and water (100 ml) and the organic phase was dried over magnesium sulphate. Solvent evaporation in vacuo yielded 4-chloro-6-methoxy-7-benzyloxyquinazoline (4.80 g, 90% yield) as a pale brown solid:

$^1$H-NMR (DMSO d$_6$): 8.85 (s, 1H), 7.58 (s, 1H), 7.50 (d, 2H), 7.40 (m, 4H), 5.35 (s, 2H), 4.00 (s, 3H):

MS (+ve ESI): 301 (M+H)$^+$.

EXAMPLE 45

Preparation of Compound No. 45 in Table 1

An analogous reaction to that described in example 33, but starting with 2-aminoindan (66.9 mg, 0.50 mmol) yielded the title compound (189 mg, 72% yield) as a white solid:

$^1$H-NMR (DMSO d$_6$): 9.54 (s, 1H), 8.47 (s, 1H), 8.33 (d, 1H), 7.89 (d, 2H), 7.83 (s, 1H), 7.55 (d, 2H), 7.42 (d, 1H), 7.10–7.27 (m, 5H), 6.55 (d, 1H), 4.51–4.63 (m, 1H), 4.18 (t, 2H), 3.96 (s, 3H), 3.53–3.60 (m, 4H), 3.15–3.25 (m, 2H), 2.75–2.87 (m, 2H), 2.44 (t, 2H), 2.33–2.40 (m, 4H), 1.87–2.01 (m, 2H):

MS (+ve ESI): 580 (M+H)$^+$.

EXAMPLE 46

Preparation of Compound No. 46 in Table 1

An analogous reaction to that described in example 33, but starting with 2-thiophene ethylamine (63.9 mg, 0.50 mmol) yielded the title compound (272 mg, 100% yield) as a white solid:

$^1$H-NMR (DMSO d$_6$): 9.55 (s, 1H), 8.48 (s, 1H), 8.18 (t, 1H), 7.90 (d, 2H), 7.84 (s, 1H), 7.57 (d, 2H), 7.41 (d, 1H), 7.30–7.34 (m, 1H), 7.19 (s, 1H), 6.87–6.97 (m, 2H), 6.55 (d, 1H), 4.19 (t, 2H), 3.96 (s, 3H), 3.53–3.62 (m, 4H), 3.38–3.47 (m, 2H), 3.00 (t, 2H), 2.46 (t, 2H), 2.33–2.42 (m, 4H), 1.89–2.01 (m, 2H):

MS (+ve ESI): 574 (M+H)$^+$.

EXAMPLE 47

Preparation of Compound No. 47 in Table 1

An analogous reaction to that described in example 33, but starting with 5-methyl-2-(aminomethyl)furan (55.9 mg, 0.50 mmol) yielded the title compound (191 mg, 76% yield) as a white solid:

$^1$H-NMR (300 MHz, DMSO d$_6$): 9.54 (s, 1H), 8.48 (s, 1H), 8.43 (t, 1H), 7.90 (d, 2H), 7.84 (s, 1H), 7.56 (d, 2H), 7.43 (d, 1H), 7.20 (s, 1H), 6.59 (d, 1H), 6.13 (d, 1H), 5.98 (d, 1H), 4.33 (d, 2H), 4.19 (t, 2H), 3.97 (s, 3H), 3.52–3.61 (m, 4H), 2.45 (t, 2H), 2.31–2.41 (m, 4H), 2.23 (s, 3H), 1.88–2.02 (m, 2H):

MS (+ve ESI): 558 (M+H)$^+$.

EXAMPLE 48

Preparation of Compound No. 48 in Table 1

An analogous reaction to that described in example 33, but starting with 3-aminotetrahydrothiophene-1,1'-dioxide dihydrochloride (104.5 mg, 0.50 mmol) yielded the title compound (253 mg, 96% yield) as a white solid:

$^1$H-NMR (DMSO d$_6$): 9.55 (s, 1H), 8.50 (s, 1H), 8.49 (d, 1H), 7.92 (d, 2H), 7.84 (s, 1H), 7.59 (d, 2H), 7.45 (d, 1H), 7.18 (s, 1H), 6.52 (d, 1H), 4.50–4.65 (m, 1H), 4.19 (t, 2H), 3.96 (s, 3H), 3.53–3.61 (m, 4H), 3.40–3.50 (m, 1H), 3.10–3.35 (m, 2H), 2.89–2.98 (m, 1H), 2.32–2.53 (m, 1H), 2.45 (t, 2H), 2.32–2.41 (m, 4H), 2.01–2.18 (m, 1H), 1.88–2.01 (m, 2H):

MS (+ve ESI): 582 (M+H)$^+$.

EXAMPLE 49

Preparation of Compound No. 49 in Table 1

An analogous reaction to that described in example 33, but starting with 2-(methylthio)ethylamine (45.8 mg, 0.50 mmol) yielded the title compound (166.6 mg, 68% yield) as a white solid:

$^1$H-NMR (DMSO d$_6$): 9.56 (s, 1H), 8.49 (s, 1H), 7.89 (d, 2H, J=8 Hz), 7.85 (s, 1H), 7.59 (d, 2H, J=8 Hz), 7.41 (d, 1H, J=16 Hz), 7.19 (s, 1H), 6.56 (d, 1H, J=16 Hz), 4.19 (t, 2H, J=7 Hz), 3.97 (s, 3H), 3.53–3.61 (m, 4H), 3.31–3.40 (m, 2H), 2.59 (t, 2H, J=7 Hz), 2.45 (t, 2H, J=7 Hz), 2.32–2.41 (m, 4H), 2.09 (s, 3H), 1.88–2.01 (m, 2H):

MS (+ve ESI): 538 (M+H)$^+$.

EXAMPLE 50

Preparation of Compound No. 50 in Table 1

A solution of 1.0N hydrochloric acid in ether (0.50 ml, 0.50 mmol) was added to a solution of ethyl 4-aminocinnamate (96 mg, 0.50 mmol) and 4-chloro-6-methoxy-7-(3-morpholinopropoxy)quinazoline (168 mg, 0.50 mmol), in isopropanol (5.0 ml). The reaction was heated at 40° C. for 30 minutes and then at 83° C. for 12 hours. The reaction was allowed to cool to ambient temperature and the solid which had precipitated was collected by suction filtration and washed with diethyl ether (2×10 ml). Drying of this material yielded the title compound (248 mg, 94% yield) as a white solid:

$^1$H-NMR (DMSO d$_6$): 11.55 (s, 1H), 11.10 (s, 1H), 8.88 (s, 1H), 8.50 (s, 1H), 7.85 (m, 4H), 7.68 (d, 1H, J=16 Hz), 7.45 (s, 1H), 6.63 (d, 1H, J=16 Hz), 4.30 (t, 2H), 4.20 (q, 2H), 4.05 (s, 3H), 3.98 (m, 2H), 3.82 (m, 2H), 3.45 (m, 2H), 3.30 (m, 2H), 3.10 (m, 2H), 2.35 (m, 2H), 1.25 (t, 3H):

MS (+ve ESI): 493 (M+H)$^+$.

EXAMPLE 51

Preparation of Compound No. 51 in Table 1

4-(4-(2-carboxy)ethenyl)anilino)-6-methoxy-7-(2,2,2-trifluoroethoxy)quinazoline hydrochloride (132 mg, 0.40 mmol) and 2-(methylthio)ethylamine (40 mg, 0.44 mmol) were added to a solution of 4-(dimethylamino)pyridine (98 mg, 0.8 mmol) and 1-(3-dimethylamino-propyl)-3-ethylcarbodiimide hydrochloride (84 mg, 0.44 mmol) in dimethylacetamide (5 ml). The reaction was stirred at ambient temperature for 24 hours and then heated at 70° C. for 2 hours. The reaction was cooled, water (10 ml) was added and the reaction allowed to stand overnight. The solid which precipitated was collected by suction filtration and purified by flash chromatography on silica gel, eluting with 0–10% methanol in dichloromethane. Solvent evaporation in vacuo, yielded the title compound (84 mg, 43%) as an off-white solid:

HPLC/LCMS (RT): 2.18 min:
MS (+ve ESI): 493 (M+H)$^+$.

4-(4-(2-carboxy)ethenyl)anilino)-6-methoxy-7-(2,2,2-tirfluoroethoxy)quinazoline hydrochloride, used as starting material was obtained as follows:

a) Potassium carbonate (62.2 g, 450 mmol) was added to a solution of ethyl vanillate (58.9 g, 300 mmol) in dimethylformamide (400 ml) and the reaction heated to 120° C. 2,2,2-Trifluoroethyl methanesulphonate (63.4 g, 360 mmol) was added over 15 minutes and the reaction heated at 120° C. for 15 hours. The reaction was cooled to ambient temperature, diethyl ether (400 ml) was added and the reaction was filtered. The filtrate was evaporated in vacuo and the residue was taken up in a mixture of diethyl ether (375 ml) and isohexane (375 ml). The organic layer was concentrated in vacuo to a total volume of 250 ml and the solid which crystallised out was collected by suction filtration. Drying of the solid in vacuo yielded ethyl 4-(2,2,2-trifluoroethoxy)-3-methoxybenzoate (43.0 g, 52% yield) as a white crystalline solid:

$^1$H-NMR (DMSO d$_6$): 7.57 (dd, 1H, J=2, 8 Hz), 7.49 (d, 1H, J=2 Hz), 7.18 (d, 1H, J=8 Hz), 5.81 (q, 2H, J=7 Hz), 5.29 (q, 2H, J=7 Hz), 3.82 (s, 3H), 1.30 (t, 3H, J=7 Hz):

MS (+ve ESI): 279 (M+H)$^+$.

b) Concentrated sulphuric acid (64 ml) and concentrated nitric acid (10.0 ml, 0.152 mol) were added cautiously, over 1 hour, to a two-phase system containing a stirred solution of ethyl 4-(2,2,2-trifluoroethoxy)-3-methoxybenzoate (35.3 g, 0.127 mol) in dichloromethane (340 ml), acetic acid (173 ml) and water (40 ml) at 5° C. The reaction was allowed to warm to ambient temperature over 60 hours (with vigorous mechanical stirring), the aqueous phase was separated, and the organic phase washed with water (6×250 ml). The organic phase was concentrated to a total volume of ~200 ml, isohexane (150 ml) was added and the solid which precipitated was collected by suction filtration. Drying of the solid in vacuo yielded ethyl 3-methoxy-4-(2,2,2-tirfluoroethoxy)-6-nitrobenzoate (21.7 g, 52% yield) as a yellow solid. The mother liquors contained a mixture of product (28%) and starting material (72%) which was recycled in a latter reaction:

$^1$H-NMR (DMSO d$_6$): 7.80 (s, 1H), 7.42 (s, 1H), 4.90 (q, 2H, J=7 Hz), 4.20–4.35 (m, 2H), 4.00 (s, 3H), 1.32 (t, 3H, J=7 Hz):

MS (+ve ESI): 324 (M+H)$^+$.

c) A suspension of ethyl 3-methoxy-4-(2,2,2-trifluoroethoxy)-6-nitrobenzoate (24.0 g, 74.3 mmol) and 10% palladium on carbon (3.0 g) in a mixture of ethanol (100 ml) and ethyl acetate (750 ml) was stirred under an atmosphere of hydrogen for 18 hours. Removal of the catalyst by filtration, followed by solvent evaporation in vacuo yielded ethyl 3-methoxy-4-(2,2,2-trifluoroethoxy)-6-aminobenzoate (20.2 g, 93% yield) as a pale brown solid:

$^1$H-NMR (DMSO d$_6$): 7.20 (s, 1H), 6.45 (s, 1H), 6.40 (s, 2H), 5.70 (q, 2H, J=7 Hz), 4.20 (q, 2H, J=7 Hz), 3.65 (s, 3H), 1.32 (t, 3H, J=7 Hz):

MS (−ve ESI): 292 (M−H)$^-$,
MS (+ve ESI): 294 (M+H)$^+$.

d) A mixture of ethyl 2-amino-4-(2,2,2-trifluoroethoxy)-5-methoxybenzoate (20.2 g, 69.1 mmol) and formamide (50 ml) was heated at 175° C. for 6 hours. The mixture was allowed to cool to ambient temperature, ethanol (150 ml) was added and the reaction allowed to stand for 18 hours. Collection of the solid which had precipitated by suction filtration, followed by washing with ethanol (2×50 ml) and drying in vacuo, yielded 6-methoxy-7-(2,2,2-trifluoroethoxy)-3,4-dihydroquinazolin-4-one (15.8 g, 84% yield) as a pale brown crystalline solid:

$^1$H-NMR (DMSO d$_6$): 12.10 (s, 1H), 8.00 (s, 1H), 7.51 (s, 1H), 7.30 (s, 1H), 4.90 (q, 2H, J=7 Hz), 3.90 (s, 3H):

MS (−ve ESI): 273 (M−H)$^-$,
MS (+ve ESI): 275 (M+H)$^+$.

e) Dimethylformamide (0.1 ml) was added dropwise to a solution of 6-methoxy-7-(2,2,2-trifluoroethoxy)-3,4-dihydroquinazolin-4-one (15.8 g, 57.7 mmol) in thionyl chloride (200 ml) and the reaction was heated at reflux for 6 hours.

The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6-methoxy-7-(2,2,2-trifluoroethoxy)quinazoline (16.3 g, 97% yield) as a cream solid:

$^1$H-NMR (DMSO $d_6$): 8.95 (s, 1H), 7.65 (s, 1H), 7.25 (s, 1H), 5.05 (q, 2H, J=7 Hz), 4.00 (s, 3H):
MS (+ve ESI): 293, 295 (M+H)$^+$.

f) An analogous reaction to that described in example 3c, but starting with 4-chloro-6-methoxy-7-(2,2,2-trifluoroethoxy)quinazoline (4.50 g, 15.4 mmol) and 4-aminocinnamic acid hydrochloride (3.07 g, 15.4 mmol) yielded 4-(4-(2-carboxy)ethenyl)anilino)-6-methoxy-7-(2,2,2-trifluoroethoxy)quinazoline hydrochloride (5.17 g, 74% yield) as a white solid:

$^1$H-NMR (DMSO $d_6$): 11.42 (s, 1H), 8.85 (s, 1H), 8.40 (s, 1H), 7.75–7.85 (m, 4H), 7.60 (d, 1H), 7.40 (s, 1H), 6.55 (d, 1H), 5.00–5.15 (m, 2H), 4.05 (d, 3H):
MS (+ve ESI): 293, 295 (M+H)$^+$,
MS (−ve ESI): 293, 295 (M−H)$^-$.

EXAMPLE 52

Preparation of Compound No. 52 in Table 1

An analogous reaction to that described in example 51, but starting with cyclopentylamine (37 mg, 0.44 mmol), yielded the title compound (39 mg, 20% yield) as an off-white solid:
HPLC/LCMS (RT): 2.32 min:
MS (+ve ESI): 487 (M+H)$^+$.

EXAMPLE 53

Preparation of Compound No. 53 in Table 1

An analogous reaction to that described in example 51, but starting with cyclohexylamine (44 mg, 0.44 mmol), yielded the title compound (90 mg, 45% yield) as an off-white solid:
HPLC/LCMS (RT): 2.45 min:
MS (+ve ESI): 501 (M+H)$^+$.

EXAMPLE 54

Preparation of Compound No. 54 in Table 1

An analogous reaction to that described in example 51, but starting with aminomethylcyclohexane (50 mg, 0.44 mmol), yielded the title compound (137 mg, 67% yield) as an off-white solid:
HPLC/LCMS (RT): 2.62 min:
MS (+ve ESI): 515 (M+H)$^+$.

EXAMPLE 55

Preparation of Compound No. 55 in Table 1

An analogous reaction to that described in example 51, but starting with 5-amino-2-chloropyridine (56 mg, 0.44 mmol), yielded the title compound (40 mg, 19% yield) as an off-white solid:
HPLC/LCMS (RT): 2.47 min:
MS (+ve ESI): 530 (M+H)$^+$.

EXAMPLE 56

Preparation of Compound No. 56 in Table 1

An analogous reaction to that described in example 51, but starting with furfurylamine (43 mg, 0.44 mmol), yielded the title compound (43 mg, 22% yield) as an off-white solid:
HPLC/MCMS (RT): 2.31 min:
MS (+ve ESI): 499 (M+H)$^+$.

EXAMPLE 57

Preparation of Compound No. 57 in Table 1

An analogous reaction to that described in example 51, but starting with tetrahydrofurfurylamine (44 mg, 0.44 mmol), yielded the title compound (138 mg, 69% yield) as an off-white solid:
HPLC/LCMS (RT): 2.11 min:
MS (+ve ESI): 503 (M+H)$^+$.

EXAMPLE 58

Preparation of Compound No. 58 in Table 1

An analogous reaction to that described in example 51, but starting with 3-aminopyridine (41 mg, 0.44 mmol), yielded the title compound (172 mg, 87% yield) as an off-white solid:
HPLC/LCMS (RT): 1.87 min:
MS (+ve ESI): 496 (M+H)$^+$.

EXAMPLE 59

Preparation of Compound No. 59 in Table 1

An analogous reaction to that described in example 51, but starting with ortho-toluidine (47 mg, 0.44 mmol), yielded the title compound (188 mg, 93% yield) as an off-white solid:
HPLC/LCMS (RT): 2.61 min:
MS (+ve ESI): 509 (M+H)$^+$.

EXAMPLE 60

Preparation of Compound No. 60 in Table 1

An analogous reaction to that described in example 51, but starting with 2,2,2-trifluoroethylamine (44 mg, 0.44 mmol), yielded the title compound (181 mg, 91% yield) as an off-white solid:
HPLC/LCMS (RT): 2.61 min:
MS (+ve ESI): 501 (M+H)$^+$.

EXAMPLE 61

Preparation of Compound No. 61 in Table 1

An analogous reaction to that described in example 51, but starting with 3-amino-1,2-propanediol (40 mg, 0.44 mmol), yielded the title compound (171 mg, 87% yield) as an off-white solid:
HPLC/LCMS (RT): 2.61 min:
MS (+ve ESI): 493 (M+H)$^+$.

EXAMPLE 62

Preparation of Compound No. 62 in Table 1

An analogous reaction to that described in example 51, but starting with 2-methyl-1-amylamine (44 mg, 0.44 mmol), yielded the title compound (83 mg, 41% yield) as an off-white solid:
HPLC/LCMS (RT): 2.61 min:
MS (+ve ESI): 503 (M+H)$^+$.

EXAMPLE 63

Preparation of Compound No. 63 in Table 1

An analogous reaction to that described in example 51, but starting with 3-methylcyclohexylamine (50 mg, 0.44 mmol), yielded the title compound (128 mg, 62% yield) as an off-white solid:
HPLC/LCMS (RT): 2.66 min:
MS (+ve ESI): 515 (M+H)$^+$.

EXAMPLE 64

Preparation of Compound No. 64 in Table 1

An analogous reaction to that described in example 51, but starting with 2-aminoindan (59 mg, 0.44 mmol), yielded the title compound (104 mg, 49% yield) as an off-white solid:
HPLC/LCMS (RT): 2.56 min:
MS (+ve ESI): 535 (M+H)$^+$.

EXAMPLE 65

Preparation of Compound No. 65 in Table 1

An analogous reaction to that described in example 51, but starting with 2-thiophene ethylamine (56 mg, 0.44 mmol), yielded the title compound (113 mg, 54% yield) as an off-white solid:
HPLC/LCMS (RT): 2.44 min:
MS (+ve ESI): 529 (M+H)$^+$.

EXAMPLE 66

Preparation of Compound No. 66 in Table 1

An analogous reaction to that described in example 51, but starting with 3-aminotetrahydrothiophene-1,1'-dioxide (59 mg, 0.44 mmol), yielded the title compound (162 mg, 76% yield) as an off-white solid:
HPLC/LCMS (RT): 2.09 min:
MS (+ve ESI): 537 (M+H)$^+$.

EXAMPLE 67

Preparation of Compound No. 67 in Table 1

An analogous reaction to that described in example 51, but starting benzylamine (47 mg, 0.44 mmol), yielded the title compound (137 mg, 67% yield) as an off-white solid:
$^1$H-NMR (DMSO d$_6$): 9.65 (s, 1H), 8.55 (t, 1H, J=7 Hz), 8.50 (t, 1H, J=7 Hz), 7.95 (m, 2H), 7.90 (s, 1H), 7.68 (d, 1H, J=16 Hz), 7.45 (s, 1H), 7.40 (s, 1H), 7.22–7.35 (m, 5H), 6.63 (d, 1H, J=16 Hz), 4.95 (q, 2H, J=7 Hz), 4.40 (d, 2H, J=7 Hz), 3.99 (s, 3H):
MS (+ve ESI): 509 (M+H)$^+$.

EXAMPLE 68

Preparation of Compound No. 68 in Table 1

An analogous reaction to that described in example 3c, but starting with 4-chloro-6,7-dimethoxyquinazoline (30 mg, 0.13 mmol) and cis-ethyl 4-aminocinnamate (50 mg, 0.26 mmol), and using ethanol as solvent (2 ml), yielded the title compound (36 mg, 65% yield) as a yellow solid:
$^1$H-NMR (DMSO d$_6$): 11.35 (s, 1H), 8.83 (s, 1H), 8.32 (s, 1H), 7.71–7.83 (m, 4H), 7.35 (s, 1H), 7.03 (d, 1H, J=12.6 Hz), 6.01 (d, 1H, J=12.6 Hz), 4.15 (q, 2H, J=7 Hz), 4.05 (s, 3H), 4.00 (s, 3H), 1.20 (t, 3H, J=7 Hz):
MS (+ve ESI): 380 (M+H)$^+$.

cis-Ethyl 4-aminocinnamate, used as starting material was obtained as follows:

a) Palladium (II) bis(triphenylphosphine) dichloride (140 mg, 0.20 mmol), copper (I) iodide (76 mg, 0.40 mmol) and potassium carbonate (2.8 g, 20 mmol) were added to a solution of 4-iodo-nitrobenzene (2.49 g, 10.0 mmol) and ethyl propiolate (3.92 g, 40 mmol) in tetrahydrofuran (30 ml) and the reaction heated at reflux for 16 hours under an inert atmosphere. The reaction was cooled to ambient temperature, poured into water (150 ml), diluted with ethyl acetate (75 ml) and filtered through celite. The organic layer was separated, the aqueous was extracted with ethyl acetate (2×100 ml) and the combined organic layers were dried over magnesium sulphate before solvent evaporation in vacuo. Purification by flash chromatography on silica gel, eluting with 25% ethyl acetate in isohexane, yielded ethyl 2-(4-nitrophenyl)propiolate (1.55 g, 71% yield) as a yellow solid:
$^1$H-NMR (DMSO d$_6$): 8.25–8.30 (m, 2H), 7.90–7.95 (m, 2H), 4.25 (q, 2H, J=7 Hz), 1.25 (t, 3H):
MS (+ve ESI): 219 (M+H)$^+$.

b) Iron powder (276 mg, 5.0 mmol) and ammonium chloride (266 mg, 5.0 mmol) were added to a solution of ethyl 2-(4-nitrophenyl)propiolate (110 mg, 0.50 mmol) in a mixture of water (5 ml) and ethanol (5 ml) and the reaction heated at reflux for 5 hours under an inert atmosphere. The reaction was filtered through celite, the filtrate was concentrated in vacuo and the residue partitioned between water and ethyl acetate. The organic layer was separated and dried over magnesium sulphate. Purification by flash chromatography on silica gel, eluting with 33% ethyl acetate in isohexane, yielded cis-ethyl 4-aminocinnamate (50 g, 53% yield) as a brown oil:
MS (−ve ESI): 190 (M−H)$^-$,
MS (+ve ESI): 192 (M+H)$^+$.

Biological Data

The compounds of the invention inhibit the serine/threonine kinase activity of the aurora2 kinase and thus inhibit the cell cycle and cell proliferation. These properties may be assessed, for example, using one or more of the procedures set out below:

(a) In Vitro Aurora2 Kinase Inhibition Test

This assay determines the ability of a test compound to inhibit serine/threonine kinase activity. DNA encoding aurora2 may be obtained by total gene synthesis or by cloning. This DNA may then be expressed in a suitable expression system to obtain polypeptide with serine/threonine kinase activity. In the case of aurora2, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5'

PCR primer contained a recognition sequence for the restriction endonuclease BamH1 5' to the aurora2 coding sequence. This allowed the insertion of the aurora2 gene in frame with the 6 histidine residues, spacer region and rTEV protease cleavage site encoded by the pFastBac HTc vector. The 3' PCR primer replaced the aurora2 stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged aurora2 protein. Details of the methods for the assembly of recombinant DNA molecules can be found in standard texts, for example Sambrook et al. 1989, Molecular Cloning—A Laboratory Manual, $2^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora2 gene was transformed into E. coli DH10Bac cells containing the baculovirus genome (bacmid DNA) and via a transposition event in the cells, a region of the pFastBac vector containing gentamycin resistance gene and the aurora2 gene including the baculovirus polyhedrin promoter was transposed directly into the bacmid DNA. By selection on gentamycin, kanamycin, tetracycline and X-gal, resultant white colonies should contain recombinant bacmid DNA encoding aurora2. Bacmid DNA was extracted from a small scale culture of several BH10Bac white colonies and transfected into Spodoptera frugiperda Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1 \times 10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant aurora2 protein.

For the large scale expression of aurora2 kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure aurora2 recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (25 mM HEPES (N-[2-hydroxyethyl]piperazine-N'-[2-ethanesulphonic acid]) pH7.4 and 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 μg/ml aprotinin, 1 μg/ml pepstatin, 1 μg/ml leupeptin), using 1.0 ml per $3 \times 10^7$ cells. Lysis was achieved using a dounce homogeniser, following which the lysate was centrifuged at 41,000 g for 35 minutes. Aspirated supernatant was pumped onto a 5 mm diameter chromatography column containing 500 μl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora2 protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora2 kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of aurora2 enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent & 20 μl of dilute enzyme is used for each assay well. Test compounds (at 10 mM in dimethylsulphoxide (DMSO)) were diluted with water & 10 μl of diluted compound was transferred to wells in the assay plates. "Total" & "blank" control wells contained 2.5% DMSO instead of compound. Twenty microliters of freshly diluted enzyme was added to all wells, apart from "blank" wells. Twenty microliters of enzyme diluent was added to "blank" wells. Twenty microliters of reaction mix (25 mM Tris-HCl, 78.4 mM KCl, 2.5 mM NaF, 0.6 mM dithiothreitol, 6.25 mM MnCl$_2$, 6.25 mM ATP, 7.5 μM peptide substrate [biotin-LRRWSLGLRRWS-LGLRRWSLGLRRWSLG]) containing 0.2 μCi [γ$^{33}$P]ATP (Amersham Pharmacia, specific activity≧2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity.

In this test, compound 18 in Table 1 gave 50% inhibition of enzyme activity at a concentration of 0.117 μM.

(b) In Vitro Cell Proliferation Assay

These and other assays can be used to determine the ability of a test compound to inhibit the growth of adherent mammalian cell lines, for example the human tumour cell line MCF7.

Assay 1

MCF-7 (ATCC HTB-22) or other adherent cells were typically seeded at $1 \times 10^3$ cells per well (excluding the peripheral wells) in DMEM (Sigma Aldrich) without phenol red, plus 10% foetal calf serum, 1% L-glutamine and 1% penicillin/streptomycin in 96 well tissue culture treated clear plates (Costar). The following day (day 1), the media was removed from a no treatment control plate and the plate stored at −80° C. The remaining plates were dosed with compound (diluted from 10 mM stock in DMSO using DMEM (without phenol red, 10% FCS, 1% L-glutamine, 1% penicillin/streptomycin). Untreated control wells were included on each plate. After 3 days in the presence/absence of compound (day 4) the media was removed and the plates stored at −80° C. Twenty four hours later the plates were thawed at room temperature and cell density determined using the CyQUANT cell proliferation assay kit (c-7026/c-7027 Molecular Probes Inc.) according to manufacturers directions. Briefly, 200 μl of a cell lysis/dye mixture (10 μl of 20× cell lysis buffer B, 190 µl of sterile water, 0.25 µl of CYQUANT GR dye) was added to each well and the plates incubated at room temperature for 5 minutes in the dark. The fluorescence of the wells was then measured using a fluorescence microplate reader (gain 70, 2 reads per well, 1 cycle with excitation 485 nm and emission 530 nm using a CytoFluor plate reader (PerSeptive Biosystems Inc.)). The values from day 1 and day 4 (compound treated) together with the values from the untreated cells were used to determine the dilution range of a test compound that gave 50% inhibition of cell proliferation. Compound 18 in Table 1 was effective in this test at 6.38 µM.

These values could also be used to calculate the dilution range of a test compound at which the cell density dropped below the day 1 control value. This indicates the cytotoxicity of the compound.

Assay 2

This assay determines the ability of a test compound to inhibit the incorporation of the thymidine analogue, 5'-bromo-2'-deoxy-uridine (BrdU) into cellular DNA. MCF-7 or other adherent cells were typically seeded at 0.8×10⁴ cells per well in DMEM (Sigma Aldrich) without phenol red, plus 10% foetal calf serum, 1% L-glutamine and 1% penicillin/streptomycin (50 µl/well) in 96 well tissue culture treated 96 well plates (Costar) and allowed to adhere overnight. The following day the cells were dosed with compound (diluted from 10 mM stock in DMSO using DMEM (without phenol red, 10% FCS, 1% L-glutamine, 1% penicillin/streptomycin). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 µl of BrdU labelling reagent (diluted 1:100 in media—DMEM no phenol red, 10% FCS, 1% L-glutamine, 1% penicillin/streptomycin) was added to each well and the plate returned to a humidified (+5% $CO_2$) 37° C. incubator for 2 hours. After 2 hours the labelling reagent was removed by decanting and tapping the plate on a paper towel. FixDenat solution (50 µl per well) was added and the plates incubated at room temperature for 45 mins with shaking. The FixDenat solution was removed by decanting and tapping the inverted plate on a paper towel. The plate was then washed once with phosphate buffered saline (PBS) and 100 µl/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 5 times with PBS before being blotted dry. TMB substrate solution was added (100 µl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. Compound 18 in Table 1 was effective in this test at 2.47 µM (c) In Vitro Cell Cycle Analysis Assay This assay determines the ability of a test compound to arrest cells in specific phases of the cell cycle. Many different mammalian cell lines could be used in this assay and MCF7 cells are included here as an example. MCF-7 cells were seeded at 3×10⁵ cells per T25 flask (Costar) in 5 ml DMEM (no phenol red 10% FCS, 1% L-glutamine 1% penicillin/streptomycin). Flasks were then incubated overnight in a humidified 37° C. incubator with 5% $CO_2$. The following day 1 ml of DMEM (no phenol red 10% FCS, 1% L-glutamine 1% penicillin/streptomycin) carrying the appropriate concentration of test compound solubilised in DMSO was added to the flask. A no compound control treatments was also included (0.5% DMSO). The cells were then incubated for a defined time (usually 24 hours) with compound. After this time the media was aspirated from the cells and they were washed with 5 ml of prewarmed (37° C.) sterile PBSA, then detached from the flask by brief incubation with trypsin and followed by resuspension in 10 ml of 1% Bovine Serum Albumin (BSA, Sigma-Aldrich Co.) in sterile PBSA. The samples were then centrifuged at 2200 rpm for 10 min. The supernatant was aspirated and the cell pellet was resuspended in 200 µl of 0.1% (w/v) Tris sodium citrate, 0.0564% (w/v) NaCl, 0.03% (v/v) Nonidet NP40, [pH 7.6]. Propridium Iodide (Sigma Aldrich Co.) was added to 40 µg/ml and RNAase A (Sigma Alrich Co.) to 100 µg/ml. The cells were then incubated at 37° C. for 30 minutes. The samples were centrifuged at 2200 rpm for 10 min, the supernatant removed and the remaining pellet (nuclei) resuspended in 200 µl of sterile PBSA. Each sample was then syringed 10 times using 21 gauge needle. The samples were then transferred to LPS tubes and DNA content per cell analysed by Fluorescence activated cell sorting (FACS) using a FACScan flow cytometer (Becton Dickinson). Typically 25000 events were counted and recorded using CellQuest v1.1 software (Verity Software). Cell cycle distribution of the population was calculated using Modfit software (Verity Software) and expressed as percentage of cells in G0/G1, S and G2/M phases of the cell cycle. Treating MCF7 cells with 12.76 µM Compound 18 in Table 1 for 24 hours produced the following changes in cell cycle distribution:

| Treatment | % Cells in G1 | % Cells in S | % Cells in G2/M |
| --- | --- | --- | --- |
| DMSO (control) | 65.58 | 22 | 9.81 |
| 12.76 µM Compound 18 | 30.96 | 19.42 | 49.62 |

The invention claimed is:
1. A compound of formula (I)

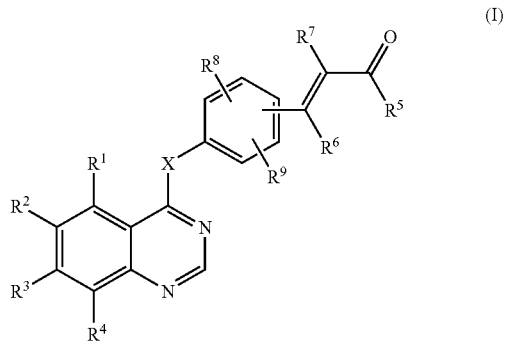

or a salt, or phosphate ester thereof;
where X is O, or S, S(O) or S(O)₂ or NR¹⁰ where R¹⁰ is hydrogen or $C_{1-6}$alkyl;

$R^5$ is a group $OR^{11}$, $NR^{12}R^{13}$ or $SR^{11}$ where $R^{11}$, $R^{12}$ and $R^{13}$ are independently selected from hydrogen, optionally substituted hydrocarbyl where optional substituents are functional groups, or optionally substituted heterocyclic groups where optional substituents are functional groups or hydrocarbyl, and $R^{12}$ and $R^{13}$ may additionally form together with the nitrogen atom to which they are attached, an optionally substituted aromatic or non-aromatic heterocyclic ring which may contain further heteroatoms;

$R^6$ and $R^7$ are independently selected from hydrogen or hydrocarbyl;

$R^8$ and $R^9$ are independently selected from hydrogen, halo, $C_{1-4}$alkyl, $C_{1-4}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms selected independently from O, S and N, which heterocyclic group may be aromatic or non-aromatic and may be saturated, linked via a ring carbon or nitrogen atom, or unsaturated, linked via a ring carbon atom, and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl; and $R^1$, $R^2$, $R^3$, $R^4$ are independently selected from halogeno, cyano, nitro, $C_{1-3}$alkylsulphanyl, —N(OH)$R^{14}$ wherein $R^{14}$ is hydrogen or $C_{1-3}$alkyl, or $R^{16}X^1$— wherein $X^1$ represents a direct bond, —O—, —CH$_2$—, —OC(O)—, —C(O)—, —S—, —SO—, —SO$_2$—, —NR$^{17}$C(O)—, —C(O)NR$^{18}$—, —SO$_2$NR$^{19}$—, —NR$^{20}$SO$_2$— or —NR$^{21}$—, wherein $R^{17}$, $R^{18}$, $R^{19}$, $R^{20}$ and $R^{21}$ each independently represents hydrogen, $C_{1-3}$alkyl or $C_{1-3}$alkoxyC$_{2-3}$alkyl, and $R^{16}$ is selected from one of the following twenty-two groups;

1) hydrogen or $C_{1-5}$alkyl which may be unsubstituted or which may be substituted with one or more groups selected from hydroxy, oxiranyl, fluoro, chloro, bromo, amino, $C_{1-3}$alkyl, and trifluoromethyl;

2) —R$^3$X$^2$C(O)R$^{22}$; wherein $X^2$ represents —O— or —NR$^{23}$—, in which $R^{23}$ represents hydrogen, $C_{1-3}$alkyl or $C_{1-3}$alkoxyC$_{2-3}$alkyl) and $R^{22}$ represents $C_{1-3}$alkyl, —NR$^{24}$R$^{25}$ or —OR$^{26}$, wherein $R^{24}$, $R^{25}$ and $R^{26}$ which may be the same or different each represents hydrogen, $C_{1-5}$alkyl, hydroxyC$_{1-5}$alkyl or $C_{1-3}$alkoxyC$_{2-3}$alkyl;

3) —R$^b$X$^3$R$^{27}$; wherein $X^3$ represents —O—, C(O)—S—, —SO—, —SO$_2$—, —OC(O)—, —NR$^{28}$C(O)—, —NR$^{28}$C(O)O—, —C(O)NR$^{29}$—, C(O)ONR$^{29}$—, —SO$_2$NR$^{30}$—, —NR$^{31}$SO$_2$— or 'NR$^{32}$—, wherein $R^{28}$, $R^{29}$, $R^{30}$, $R^{31}$ and $R^{32}$ each independently represents hydrogen, $C_{1-3}$alkyl, hydroxy $C_{1-3}$alkyl or $C_{1-3}$alkoxyC$_{2-3}$alkyl, and $R^{27}$ represents hydrogen, $C_{1-6}$alkyl, $C_{2-6}$alkenyl, cyclopropyl, cyclobutyl, cyclopentyl, cyclohexyl, phenyl or a 5–6-membered saturated heterocyclic group with 1–2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, $C_{1-4}$alkanoyldi-$C_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)amino $C_{1-4}$alkoxy and a group —(—O—)$_f$(R$^{b'}$)$_g$D, wherein f is 0 or 1, q is 0 or 1 and D is a cyclic group selected from $C_{3-6}$cycloalkyl group, an aryl group or a 5–6-membered saturated or unsaturated heterocyclic group with 1–2 heteroatoms, selected independently from O, S and N, which cyclic group may bear one or more substituents selected from halo or $C_{1-4}$alkyl;

4) —R$^c$X$^4$R$^{c'}$X$^5$R$^{35}$; wherein $X^4$ and $X^5$ which may be the same or different are each —O—, C(O), —S—, —SO—, —SO$_2$—, —NR$^{36}$C(O)—, —NR$^{36}$C(O)O—, —C(O)NR$^{37}$—, —C(O)ONR$^{37}$—, —SO$_2$NR$^{38}$—, —NR$^{39}$SO$_2$— or —NR$^{40}$—, wherein $R^{36}$, $R^{37}$, $R^{38}$, $R^{39}$ and $R^{40}$ each independently represents hydrogen, $C_{1-3}$alkyl or $C_{1-3}$alkoxyC$_{2-3}$alkyl, and $R^{35}$ represents hydrogen, $C_{1-3}$alkyl, hydroxyC$_{1-3}$alkyl or $C_{1-3}$alkoxyC$_{2-3}$alkyl;

5) $R^{41}$; wherein $R^{41}$ is a 4–6-membered cycloalkyl or saturated heterocyclic ring, linked via carbon or nitrogen, with 1–2 heteroatoms, selected independently form O, S and N, which cycloalkyl or heterocyclic group may bear 1 or 2 substituents selected from oxo, hydroxy, halogeno, cyano, $C_{1-4}$alkyl, hydroxy $C_{1-4}$alkyl, cyanoC$_{1-4}$alkyl, cyclopropyl, $C_{1-4}$alkylsulphonylC$_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylaminoC$_{1-4}$alkyl, $C_{1-4}$alkanoyl, di($C_{1-4}$alkyl) aminoC$_{1-4}$alkyl, $C_{1-4}$alkylaminoC$_{1-4}$alkoxy, di($C_{1-4}$alkyl)aminoC$_{1-4}$alkoxy nitro, amino, $C_{1-4}$alkoxy, $C_{1-4}$hydroxyalkoxy, carboxy, trifluoromethyl, —C(O)NR$^{43}$R$^{44}$, —NR$^{45}$C(O)R$^{46}$, wherein $R^{43}$, $R^{44}$, $R^{45}$ and $R^{46}$, which may be the same or different, each represents hydrogen, $C_{1-4}$alkyl, hydroxyC$_{1-4}$alkyl or $C_{1-3}$alkoxyC$_{2-3}$alkyl) and a group —(—O—)$_f$(C$_{1-4}$alkyl)$_g$ringD, wherein f is 0 or 1, g is 0 or 1 and D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl;

6) —R$^d$R$^{41}$; wherein $R^{41}$ is as defined hereinbefore;

7) —R$^e$R$^{41}$; wherein $R^{41}$ is as defined hereinbefore;

8) —R$^f$R$^{41}$; wherein $R^{41}$ is as defined hereinbefore;

9) $R^{42}$; wherein $R^{42}$ represents a phenyl group or a 5–6-membered aromatic heterocyclic group, linked via carbon or nitrogen, with 1–3 heteroatoms selected from O, N and S, which phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyanoC$_{1-4}$alkyl, cyclopropyl, $C_{1-4}$alkylsulphonylC$_{1-4}$alkyl, $C_{1-4}$alkoxycarbonyl, di($C_{1-4}$alkyl)amino, $C_{1-4}$alkylaminoC$_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxamido, trifluoromethyl, cyano, —C(O)NR$^{69}$R$^{70}$, —NR$^{71}$C(O)R$^{72}$, wherein R$^{69}$, R$^{70}$, R$^{71}$ and R$^{72}$, which may be the same or different, each represents hydrogen, $C_{1-4}$alkyl, hydroxy$C_{1-4}$alkyl or $C_{1-3}$alkoxy$C_{2-3}$alkyl, and a group —(—O—)$_f$($C_{1-4}$alkyl)$_g$ringD, wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl;

10) —R$^g$R$^{42}$; wherein R$^{42}$ is as defined hereinbefore;
11) —R$^h$R$^{42}$; wherein R$^{42}$ is as defined hereinbefore;
12) —R$^i$R$^{42}$; wherein R$^{42}$ is as defined hereinbefore;
13) —R$^j$X$^6$R$^{42}$; wherein X$^6$ represents —O—, —C(O)—, —S—, —SO—, —SO$_2$—, —OC(O)—, —NR$^{47}$C(O)—, —C(O)NR$^{48}$—, C(O)ONR$^{48}$—, —SO$_2$NR$^{49}$—, —NR$^{50}$SO$_2$— or —NR$^{51}$—, wherein R$^{47}$, R$^{48}$, R$^{49}$, R$^{50}$ and R$^{51}$ each independently represents hydrogen, $C_{1-3}$alkyl, hydroxy$C_{1-3}$alkyl or $C_{1-3}$alkoxy$C_{2-3}$alkyl, and R$^{42}$ is as defined hereinbefore;
14) —R$^k$X$^7$R$^{42}$; wherein X$^7$ represents —O—, C(O), —S—, —SO—, —SO$_2$—, —NR$^{73}$C(O)—, —C(O)NR$^{74}$—, C(O)ONR$^{74}$—, —SO$_2$NR$^{75}$—, —NR$^{76}$SO$_2$— or —NR$^{77}$—, wherein R$^{73}$, R$^{74}$, R$^{75}$, R$^{76}$ and R$^{77}$ each independently represents hydrogen, $C_{1-3}$alkyl, hydroxy$C_{1-3}$alkyl or $C_{1-3}$alkoxy$C_{2-3}$alkyl, and R$^{42}$ is as defined hereinbefore;
15) —R$^m$X$^8$R$^{42}$; wherein X$^8$ represents —O—, —(CO)—, —S—, —SO—, —SO$_2$—, —NR$^{57}$C(O)—, —C(O)NR$^{58}$—, —SO$_2$NR$^{59}$—, —NR$^{60}$SO$_2$— or —NR$^{61}$—, wherein R$^{57}$, R$^{58}$, R$^{59}$, R$^{60}$ and R$^{61}$ each independently represents hydrogen, $C_{1-3}$alkyl, hydroxy$C_{1-3}$alkyl or $C_{1-3}$alkoxy$C_{2-3}$alkyl, and R$^{42}$ is as defined hereinbefore;
16) —R$^n$X$^9$R$^{n'}$R$^{42}$; wherein X$^9$ represents —O—, —C(O)—, —S—, —SO—, —SO$_2$—, —NR$^{62}$C(O)—, —C(O)NR$^{63}$—, C(O)ONR$^{63}$—, —SO$_2$NR$^{64}$—, —NR$^{65}$SO$_2$— or —NR$^{66}$—, wherein R$^{62}$, R$^{63}$, R$^{64}$, R$^{65}$ and R$^{66}$ each independently represents hydrogen, $C_{1-3}$alkyl, hydroxy$C_{1-3}$alkyl or $C_{1-3}$alkoxy$C_{2-3}$alkyl, and R$^{42}$ is as defined hereinbefore;
17) —R$^p$X$^9$—R$^{p'}$1R$^{41}$; wherein X$^9$ and R$^{41}$ are as defined hereinbefore;
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
20) —R'X$^9$R'R$^{41}$; wherein X$^9$ and R$^{41}$ are as defined hereinbefore;
21) —R$^u$X$^9$R$^u$R$^{41}$; wherein X$^9$ and R$^{41}$ are as defined hereinbefore; and
22) —R'R$^{67}$(R$^{v'}$)$_q$(X$^9$)$_r$R$^{68}$; wherein X$^9$ is as defined hereinbefore, q is 0 or 1, r is 0 or 1, and R$^{67}$ is a $C_{1-3}$alkylene group or a cyclic group selected from cyclopropyl, cyclobutyl, cyclopentylene, cyclohexylene or a 5–6-membered saturated heterocyclic group with 1–2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD, wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl; and R$^{68}$ is hydrogen, $C_{1-3}$alkyl, or a cyclic group selected from cyclopropyl, cyclobutyl, cyclopentyl, cyclohexyl and a 5–6-membered saturated heterocyclic group with 1–2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)$_f$($C_{1-4}$alkyl)$_g$ringD, wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl;

and wherein R$^a$, R$^b$, R$^{b'}$, R$^c$, R$^{c'}$, R$^d$, R$^g$, R$^j$, R$^n$, R$^{n'}$, R$^p$, R$^{p'}$, R$^{t'}$, R$^{u'}$, R$^v$ and R$^{v'}$ are independently selected from $C_{1-8}$alkylene groups optionally substituted by one or more substituents selected from hydroxy, halogeno, amino, R$^e$ R$^h$, R$^k$ and R$^t$ are independently selected from $C_{2-8}$alkenylene groups optionally substituted by one or more substituents selected from hydroxy, halogeno, amino, and R$^t$ may additionally be a bond; and R$^f$, R$^i$, R$^m$ and R$^u$ are independently selected from by $C_{2-8}$alkynylene groups optionally substituted by one or more substituents selected from hydroxy, halogeno, amino;

wherein a phosphate ester is a derivative of a hydroxy group present on one or more of R$^1$, R$^2$, R$^3$ or R$^4$;

wherein functional group refers to reactive substituents selected from nitro, cyano, halo, oxo, =CR$^{78}$R$^{79}$, C(O)$_x$R$^{77}$, OR$^{77}$, S(O)$_y$R$^{77}$, NR$^{78}$R$^{79}$, C(O)NR$^{78}$R$^{79}$, OC(O)NR$^{78}$R$^{79}$, =NOR$^{77}$, —NR$^{77}$C(O)$_x$R$^{78}$, —NR$^{77}$CONR$^{78}$R$^{79}$, —N=CR$^{78}$R$^{79}$, S(O)$_y$NR$^{78}$R$^{79}$ or —NR$^{77}$S(O)$_y$R$^{78}$ where R$^{77}$, R$^{78}$ and R$^{79}$ are independently selected from hydrogen, optionally substituted hydrocarbyl, optionally substituted heterocyclyl or optionally substituted $C_{1-10}$alkoxy, or R$^{78}$ and R$^{79}$ together form an optionally substituted ring which optionally contains further heteroatoms such as oxygen, nitrogen, S, S(O) or S(O)$_2$, where x is an integer of 1 or 2, y is 0 or an integer of 1–3; and where optional substituents for hydrocarbyl, heterocyclyl or $C_{1-10}$alkoxy groups R$^{77}$, R$^{78}$ and R$^{79}$ as well as rings formed by R$^{78}$ and R$^{79}$ are halo, perhalo$C_{1-10}$alkyl, mercapto, thio$C_{1-10}$alkyl, hydroxy, carboxy, $C_{1-10}$alkoxy, heteroaryl, heteroaryloxy, $C_{3-10}$cycloalkyl, $C_{3-10}$cycloalkenyl, $C_{3-10}$cycloalkynyl, $C_{2-10}$alkenyloxy, $C_{2-10}$alkynyloxy, $C_{1-10}$alkoxy$C_{1-10}$alkoxy, aryloxy where the aryl group may be substituted by halo, nitro or hydroxy, cyano, nitro, amino, mono- or di-$C_{1-10}$alkyl amino, oximino or $S(O)_yR^{90}$ where y is as defined above and $R^{90}$ is a $C_{1-10}$alkyl; and wherein hydrocarbyl is selected from $C_{1-10}$alkyl, $C_{2-10}$alkenyl, $C_{2-10}$alkynyl, aryl, ar$C_{1-10}$alkyl, $C_{3-10}$cycloalkyl, $C_{3-10}$cycloalkenyl or $C_{3-10}$cycloalkynyl; or $C_{1-10}$alkyl, $C_{2-10}$alkenyl or $C_{2-10}$alkynyl substituted with aryl, ar$C_{1-10}$alkyl, $C_{3-10}$cycloalkyl, $C_{3-10}$cycloalkenyl or $C_{3-10}$cycloalkynyl; or an aryl, heterocyclyl, $C_{1-10}$alkoxy, ar$C_{1-10}$alkyl, $C_{3-10}$cycloalkyl, $C_{3-10}$cycloalkenyl or $C_{3-10}$cycloalkynyl substituted with $C_{1-10}$alkyl, $C_{2-10}$alkenyl, $C_{2-10}$alkynyl or $C_{1-10}$alkoxy.

2. A compound according to claim 1, or a salt, or phosphate ester thereof; wherein $R^1$, $R^2$, $R^3$, $R^4$ are independently selected from, halo, cyano, nitro, trifluoromethyl, $C_{1-3}$alkyl, —$NR^{14}R^{15}$, wherein $R^{14}$ and $R^{15}$, which may be the same or different, each represents hydrogen or $C_{1-3}$alkyl, or —$X^1R^{16}$, wherein $X^1$ represents a direct bond, —O—, —$CH_2$—, —OCO—, carbonyl, —S—, —SO—, —$SO_2$—, —$NR^{17}CO$—, —$CONR^{18}$—, —$SO_2NR^{19}$—, —$NR^{20}SO_2$— or —$NR^{21}$—, wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl, and $R^{16}$ is selected from one of the following seventeen groups:

1') hydrogen or $C_{1-5}$alkyl which may be unsubstituted or which may be substituted with one or more groups selected from hydroxy, fluoro or amino;

2') $C_{1-5}$alkyl$X^2COR^{22}$; wherein $X^2$ represents —O— or —$NR^{23}$— in which $R^{23}$ represents hydrogen, $C_{1-3}$alkyl or $C_{1-3}$alkoxy$C_{2-3}$alkyl and $R^{22}$ represents $C_{1-3}$alkyl, —$NR^{24}R^{25}$ or —$OR^{26}$, wherein $R^{24}$, $R^{25}$ and $R^{26}$ which may be the same or different each represents hydrogen, $C_{1-3}$alkyl or $C_{1-3}$alkoxy$C_{2-3}$alkyl;

3') $C_{1-5}$alkyl$X^3R^{27}$; wherein $X^3$ represents —O—, —S—, —SO—, —$SO_2$—, —OCO—, —$NR^{28}CO$—, —$CONR^{29}$—, —$SO_2NR^{30}$—, —$NR^{31}SO_2$— or —$NR^{32}$—, wherein $R^{28}$, $R^{29}$, $R^{30}$, $R^{31}$ and $R^{32}$ each independently represents hydrogen, $C_{1-3}$alkyl or $C_{1-3}$alkoxy$C_{2-3}$alkyl, and $R^{27}$ represents hydrogen, $C_{1-3}$alkyl, cyclopentyl, cyclohexyl or a 5–6-membered saturated heterocyclic group with 1–2 heteroatoms selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy;

4') $C_{1-5}$-alkyl$X^4C_{1-5}$alkyl$X^5R^{35}$; wherein $X^4$ and $X^5$ which may be the same or different are each —O—, —S—, —SO—, —$SO_2$—, —$NR^{36}CO$—, —$CONR^{37}$—, —$SO_2NR^{38}$—, —$NR^{39}SO_2$— or —$NR^{40}$—, wherein $R^{36}$, $R^{37}$, $R^{38}$, $R^{39}$ and $R^{40}$ each independently represents hydrogen, $C_{1-3}$alkyl or $C_{1-3}$alkoxy$C_{2-3}$alkyl, and $R^{35}$ represents hydrogen or $C_{1-3}$alkyl;

5') $R^{41}$; wherein $R^{41}$ is a 5–6-membered saturated heterocyclic group, linked via carbon or nitrogen, with 1–2 heteroatoms selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl;

6') $C_{1-5}$alkyl$R^{41}$; wherein $R^{41}$ is as defined hereinbefore;

7') $C_{2-5}$alkenyl$R^{41}$; wherein $R^{41}$ is as defined hereinbefore;

8') $C_{2-5}$alkynyl$R^{41}$; wherein $R^{41}$ is as defined hereinbefore;

9') $R^{42}$; wherein $R^{42}$ represents a phenyl group or a 5–6-membered aromatic heterocyclic group, linked via carbon or nitrogen, with 1–3 heteroatoms selected from O, N and S, which phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{43}R^{44}$ and —$NR^{45}COR^{46}$, wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl;

10') $C_{1-5}$alkyl$R^{42}$; wherein $R^{42}$ is as defined hereinbefore;

11') $C_{2-5}$alkenyl$R^{42}$; wherein $R^{42}$ is as defined hereinbefore;

12') $C_{2-5}$alkynyl$R^{42}$; wherein $R^{42}$ is as defined hereinbefore;

13') $C_{1-5}$alkyl$X^6R^{42}$; wherein $X^6$ represents —O—, —S—, —SO—, —$SO_2$—, —$NR^{47}CO$—, —$CONR^{48}$—, —$SO_2NR^{49}$—, —$NR^{50}SO_2$— or —$NR^{51}$—, wherein $R^{47}$, $R^{48}$, $R^{49}$, $R^{50}$ and $R^{51}$ each independently represents hydrogen, $C_{1-3}$alkyl or $C_{1-3}$alkoxy$C_{2-3}$alkyl, and $R^{42}$ is as defined hereinbefore;

14') $C_{2-5}$alkenyl$X^7R^{42}$; wherein $X^7$ represents —O—, —S—, —SO—, —$SO_2$—, —$NR^{52}CO$—, —$CONR^{53}$—, —$SO_2NR^{54}$—, —$NR^{55}SO_2$— or —$NR^{56}$—, wherein $R^{52}$, $R^{53}$, $R^{54}$, $R^{55}$ and $R^{56}$ each independently represents hydrogen, $C_{1-3}$alkyl or $C_{1-3}$alkoxy$C_{2-3}$alkyl, and $R^{42}$ is as defined hereinbefore;

15') $C_{2-5}$alkynyl$X^8R^{42}$; wherein $X^8$ represents —O—, —S—, —SO—, —$SO_2$—, —$NR^{57}CO$—, —$CONR^{58}$—, —$SO_2NR^{59}$—, —$NR^{60}SO_2$— or —$NR^{61}$—, wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl, and $R^{42}$ is as defined hereinbefore;

16') $C_{1-3}$alkyl$X^9C_{1-3}$alkyl$R^{42}$; wherein $X^9$ represents —O—, —S—, —SO—, —$SO_2$—, —$NR^{62}CO$—, —$CONR^{63}$—, —$SO_2NR^{64}$—, —$NR^{65}SO_2$— or —$NR^{66}$—, wherein $R^{62}$, $R^{63}$, $R^{64}$, $R^{65}$ and $R^{66}$ each independently represents hydrogen, $C_{1-3}$alkyl or $C_{1-3}$alkoxy$C_{2-3}$alkyl, and $R^{42}$ is as defined hereinbefore; and 17') $C_{1-3}$alkyl$X^9C_{1-3}$alkyl$R^{41}$; wherein $X^9$ and $R^{41}$ are as defined hereinbefore;

and $R^6$ and $R^7$ are hydrogen or $C_{1-4}$alkyl.

3. A compound according to claim 2, or a salt or phosphate ester, thereof wherein $R^6$ and $R^7$ are hydrogen.

4. A compound according to claim 1 or a salt or phosphate ester thereof, wherein $R^5$ is selected from a group $OR^{11}$ where $R^{11}$ is hydrogen or $C_{1-4}$alkyl; or a group $NR^{12}R^{13}$ where one of $R^{12}$ or $R^{13}$ is hydrogen and the other is optionally substituted $C_{1-6}$alkyl, optionally substituted aryl or optionally substituted heterocyclyl, or $R^{12}$ and $R^{13}$ together with the nitrogen atom to which they are attached form a heterocyclic ring.

5. A compound according to claim 4, which is a phosphate ester of a compound of formula (I).

6. A compound according to claim 4, or a salt or phosphate ester thereof; where $R^5$ is a group $OR^{11}$, $NR^{12}R^{13}$ or $SR^{11}$ where $R^{11}$ is hydrogen or $C_{1-4}$alkyl, and where one of $R^{12}$ and $R^{13}$ is hydrogen and the other is $C_{1-6}$alkyl optionally substituted with one or more groups selected from hydroxy, trifluoromethyl, $C_{1-3}$alkoxy, cyano, amino, mono- or di-$C_{1-4}$alkylamino, $C_{1-4}$alkylthio, $C_{3-6}$cycloalkyl or heterocyclyl optionally substituted with $C_{1-4}$alkyl; or one of $R^{12}$ and $R^{13}$ is hydrogen and the other is a heterocyclic group as well as dioxides thereof, $C_{3-6}$cycloalkyl or a phenyl group any of which may be substituted with one or more groups selected from halo, nitro, $C_{1-4}$alkyl or $C_{1-4}$alkoxy, and $R^{12}$ and $R^{13}$ may additionally form together with the nitrogen atom to which they are attached, morpholine or piperidine;

$R^6$ and $R^7$ are independently selected from hydrogen or $C_{1-4}$alkyl;

$R^8$ and $R^9$ are independently selected from hydrogen, halo, $C_{1-4}$alkoxy, trifluoromethyl, cyano or phenyl.

7. A compound according to claim 6, or a salt or phosphate ester thereof, wherein X is NH or O.

8. A compound according to claim 6, or a salt or phosphate ester thereof, wherein $R^1$ is hydrogen;

$R^2$ is halo, cyano, nitro, trifluoromethyl, $C_{1-3}$alkyl, —$NR^{14}R^{15}$, wherein $R^{14}$ and $R^{15}$, which may be the same or different, each represents hydrogen or $C_{1-3}$alkyl, or a group —$X^1R^{16}$ where $X^1$ is oxygen and $R^{16}$ is a group (1);

$R^3$ is a group —$X^1R^{16}$ where $X^1$ is oxygen and $R^{16}$ is a group selected from group (1), (3), (6) and (10);

and $R^4$ is hydrogen, halo, $C_{1-4}$alkyl, or $C_{1-4}$alkoxy;

wherein group (1) is hydrogen or $C_{1-5}$alkyl which may be unsubstituted or which may be substituted with one or more groups selected from hydroxy, oxiranyl, fluoro, chloro, bromo, amino, $C_{1-3}$alkyl and trifluoromethyl;

group (3) is —$R^bX^3R^{27}$; wherein $X^3$ represents —O—, C(O)—S—, —SO—, —$SO_2$—, —OC(O)—, —$NR^{28}$C(O)—, —$NR^{28}$C(O)O—, —C(O)$NR^{29}$—, C(O) $ONR^{29}$—, —$SO_2NR^{30}$—, —$NR^{31}SO_2$— or —$NR^{32}$— wherein $R^{28}$, $R^{29}$, $R^{30}$, $R^{31}$ and $R^{32}$ each independently represents hydrogen, $C_{1-3}$alkyl, hydroxy $C_{1-4}$alkyl or $C_{1-3}$alkoxy$C_{2-3}$alkyl, and $R^{27}$ represents hydrogen, $C_{1-6}$alkyl, $C_{2-6}$alkenyl, cyclopropyl, cyclobutyl, cyclopentyl, cyclohexyl, phenyl or a 5–6-membered saturated heterocyclic group with 1–2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, $C_{1-4}$alkanoyldi-$C_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino $C_{1-4}$alkoxy and a group —(—O—)$_f$($R^{b'}$)$_q$D, wherein f is 0 or 1, q is 0 or 1 and D is a cyclic group selected from $C_{3-6}$cycloalkyl group, an aryl group or a 5–6-membered saturated or unsaturated heterocyclic group with 1–2 heteroatoms selected independently from O, S and N, which cyclic group may bear one or more substituents selected from halo or $C_{1-4}$alkyl;

group (6) is —$R^dR^{41}$; wherein $R^{41}$ is a 4–6-membered cycloalkyl or saturated heterocyclic ring, linked via carbon or nitrogen with 1–2 heteroatoms selected independently from O, S and N, which cycloalkyl or heterocyclic group may bear 1 or 2 substituents selected from oxo, hydroxy, halogeno, cyano, $C_{1-4}$alkyl, hydroxy$C_{1-4}$alkyl, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy nitro, amino, $C_{1-4}$alkoxy, $C_{1-4}$hydroxyalkoxy, carboxy, trifluoromethyl, —C(O)$NR^{43}R^{44}$, —$NR^{45}$C(O)$R^{46}$ wherein $R^{43}$, $R^{44}$, $R^{45}$ and $R^{46}$ which may be the same or different, each represents hydrogen, $C_{1-4}$alkyl, hydroxy$C_{1-4}$alkyl or $C_{1-3}$alkoxy$C_{2-3}$alkyl, and a group —(—O—)$_f$($C_{1-4}$alkyl)$_g$ringD, wherein f is 0 or 1, g is 0 or 1 and D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl;

group (10) is —$R^gR^{42}$ wherein $R^{42}$ represents a phenyl group or a 5–6-membered aromatic heterocyclic group, linked via carbon or nitrogen, with 1–3 heteroatoms selected from O, N and S, which phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$alkyl, cyclopropyl, $C_{1-4}$alkylsulphonyl $C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl) amino$C_{1-4}$alkyl, $C_{1-4}$alkylamino$C_{1-4}$alkoxy, di($C_{1-4}$ alkyl)amino$C_{1-4}$alkoxy, carboxy, carboxamido, trifluoromethyl, cyano, —C(O)$NR^{69}R^{70}$, —$NR^{71}$C(O)$R^{72}$, wherein $R^{69}$, $R^{70}$, $R^{71}$ and $R^{72}$, which may be the same or different, each represents hydrogen, $C_{1-4}$alkyl, hydroxy$C_{1-4}$alkyl or $C_{1-3}$alkoxy$C_{2-3}$alkyl, and a group —(—O—)$_f$($C_{1-4}$alkyl)$_g$ringD wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms selected independently from O, S and N, which cyclic group may bear one or more substituents selected from halo and $C_{1-4}$alkyl; and $R^b$, $R^{b'}$, $R^d$ and $R^g$ are independently selected from $C_{1-6}$alkylene groups optionally substituted by one or more substituents selected from hydroxy, halogeno, amino.

9. A compound according to claim 6, or a salt or phosphate ester thereof, wherein $R^2$ and $R^3$ are independently methoxy or 3,3,3-trifluoroethoxy.

10. A compound according to claim 6, or a salt or phosphate ester thereof, wherein $R^3$ is 3-morpholinopropoxy.

11. A compound according to claim 6, or a salt or phosphate ester thereof, wherein $R^8$ and $R^9$ are both hydrogen.

12. A compound according to claim 6, or a salt or phosphate ester thereof, wherein $R^6$ and $R^7$ are both hydrogen.

13. A compound according to claim 1 or a salt or phosphate ester thereof wherein X is NH or O.

14. A compound according to claim 1 or a salt or phosphate ester thereof wherein $R^6$ and $R^7$ are independently hydrogen or $C_{1-4}$alkyl.

15. A compound according to claim 1 or a salt or phosphate ester thereof wherein $R^8$ and $R^9$ are independently hydrogen, halo, $C_{1-4}$alkoxy, cyano, trifluoromethyl or phenyl.

16. A pharmaceutical composition comprising a compound of formula (I) as defined in claim 1, or a salt or phosphate ester thereof, in combination with a pharmaceutically acceptable carrier.

17. A method for treating colorectal or breast cancer in a warm blooded animal, in need of such treatment, which comprises administering to said animal an effective amount of a compound of formula (I), or a salt or phosphate ester thereof.

18. A method for preparing a compound of formula (I) as defined in claim 1 which method comprises reacting a compound of formula (II)

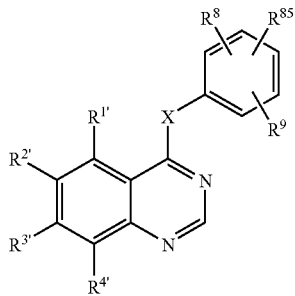

where X, $R^8$ and $R^9$ are as defined in claim 1, $R^{1'}$, $R^{2'}$, $R^{3'}$, $R^{4'}$ are groups $R^1$, $R^2$, $R^3$, $R^4$ as defined in claim 1 respectively; and $R^{85}$ is a leaving group, with a compound of formula (III)

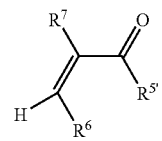

where $R^6$ and $R^7$ are as defined in claim 1 and $R^{5'}$ is a group $R^5$ as defined in claim 1.

* * * * *